US007955837B2

(12) United States Patent
Pawlak et al.

(10) Patent No.: US 7,955,837 B2
(45) Date of Patent: Jun. 7, 2011

(54) PROCESS FOR DETERMINING ONE OR MORE ANALYTES IN SAMPLES OF BIOLOGICAL ORIGIN HAVING COMPLEX COMPOSITION, AND USE THEREOF

(75) Inventors: Michael Pawlak, Nehren (DE); Eginhard Schick, Rheinfelden (DE); Miro Venturi, Basel (CH); Markus Ehrat, Magden (CH)

(73) Assignee: Bayer Technology Services GmbH, Leverkusen (DE)

( * ) Notice: Subject to any disclaimer, the term of this patent is extended or adjusted under 35 U.S.C. 154(b) by 249 days.

(21) Appl. No.: 12/084,285

(22) PCT Filed: Oct. 29, 2005

(86) PCT No.: PCT/EP2005/011607
§ 371 (c)(1), (2), (4) Date: Jul. 15, 2008

(87) PCT Pub. No.: WO2007/048436
PCT Pub. Date: May 3, 2007

(65) Prior Publication Data
US 2009/0163374 A1 Jun. 25, 2009

(51) Int. Cl.
*C12M 1/34* (2006.01)
*C12M 3/00* (2006.01)

(52) U.S. Cl. .............. 435/287.2; 435/7.1; 435/283.1; 435/287.1; 435/287.9; 435/288.3; 435/288.4; 436/518; 436/807; 436/809

(58) Field of Classification Search .............. 435/7.1, 435/283.1, 287.1, 287.2, 287.9, 288.3, 288.4; 436/518, 807, 809
See application file for complete search history.

(56) References Cited

U.S. PATENT DOCUMENTS

| 2,110,839 | A | 3/1938 | Ferriot |
| 2,182,631 | A | 12/1939 | Kenyon |
| 3,108,291 | A | 10/1963 | Eason |
| 3,138,208 | A | 6/1964 | Simms |
| 3,148,542 | A | 9/1964 | Clift, Jr. |
| 3,186,914 | A | 6/1965 | Webb et al. |
| 4,058,385 | A | 11/1977 | Kleist |
| 4,166,508 | A | 9/1979 | van den Berg |
| 4,185,576 | A | 1/1980 | George |

(Continued)

FOREIGN PATENT DOCUMENTS
AU 200068347 3/2001

(Continued)

OTHER PUBLICATIONS

C. Kappel et al., "Double Grating Waveguide Structures: 350-Fold Enhancement of Two-Photon Fluorescence Applying Ultrashort Pulses", Sensors and Actuators B, vol. 107, pp. 135-139, 2005.

(Continued)

*Primary Examiner* — Melanie J Yu
(74) *Attorney, Agent, or Firm* — Wenderoth, Lind & Ponack, LLP

(57) ABSTRACT

The present invention relates to a process for detecting one or more analytes in one or more samples of biological origin having complex composition. The present invention also relates to a microarray for quantitative determination of one or more analytes in samples of biological origin having complex composition which are immobilized in measurement ranges of microarray, and also to a quantitative detection method based thereon.

39 Claims, 11 Drawing Sheets

U.S. PATENT DOCUMENTS

| | | | |
|---|---|---|---|
| 4,487,216 A | | 12/1984 | Barker et al. |
| 5,059,014 A | | 10/1991 | Mittelhauser et al. |
| 5,158,869 A | * | 10/1992 | Pouletty et al. ................ 435/7.9 |
| 5,677,196 A | * | 10/1997 | Herron et al. ................ 436/518 |
| 5,822,472 A | | 10/1998 | Danielzik et al. |
| 5,959,292 A | | 9/1999 | Duveneck et al. |
| 6,078,705 A | | 6/2000 | Neuschafer et al. |
| 6,287,871 B1 | | 9/2001 | Herron et al. |
| 6,479,301 B1 | | 11/2002 | Balch et al. |
| 2003/0113713 A1 | * | 6/2003 | Glezer et al. ...................... 435/5 |

FOREIGN PATENT DOCUMENTS

| | | |
|---|---|---|
| EP | 0 110 012 | 1/1989 |
| WO | 95/33197 | 12/1995 |
| WO | 95/33198 | 12/1995 |
| WO | 96/35940 | 11/1996 |
| WO | 97/35181 | 9/1997 |
| WO | 98/29736 | 7/1998 |
| WO | 01/13096 | 2/2001 |
| WO | 01/43875 | 6/2001 |
| WO | 01/79821 | 10/2001 |
| WO | 01/84197 | 11/2001 |
| WO | 01/88511 | 11/2001 |
| WO | 01/92870 | 12/2001 |
| WO | 02/20873 | 3/2002 |
| WO | 02/40998 | 3/2002 |
| WO | 02/103331 | 12/2002 |
| WO | 2004/023142 | 3/2004 |
| WO | 2004/023143 | 3/2004 |

OTHER PUBLICATIONS

M. Pawlak et al., "Functional Immobilization of Biomembrane Fragments on Planar Waveguides for the Investigation of Side-Directed Ligand Binding by Surface-Confined Fluorescence", Faraday Discuss., vol. 111, pp. 273-288, 1998.

M. Pawlak et al., "Zeptosens' Protein Microarrays: A Novel High Performance Microarray Platform for Low Abundance Protein Analysis", Proteomics, vol. 2, pp. 393-393, 2002.

C. P. Paweletz et al., "Reverse Phase Protein Microarrays which Capture Disease Progression Show Activation of Pro-Survival Pathways at the Cancer Invasion Front", Oncogene, vol. 20, pp. 1981-1989, 2001.

A. Lueking et al., "Protein Microarrays for Gene Expression and Antibody Screening," Analytical Biochemistry, vol. 270, No. 1, pp. 103-111, May 1999.

M. Mullenix et al., "Allergen-specific IgE Detection on Microarrays Using Rolling Circle Amplification: Correlation with in Vitro Assays for Serum IgE," Clinical Chemistry, vol. 47, No. 10, pp. 1926-1929, 2001.

European Patent Office Search Report issued Nov. 16, 2010 in corresponding EP Application No. 10171762.7.

* cited by examiner

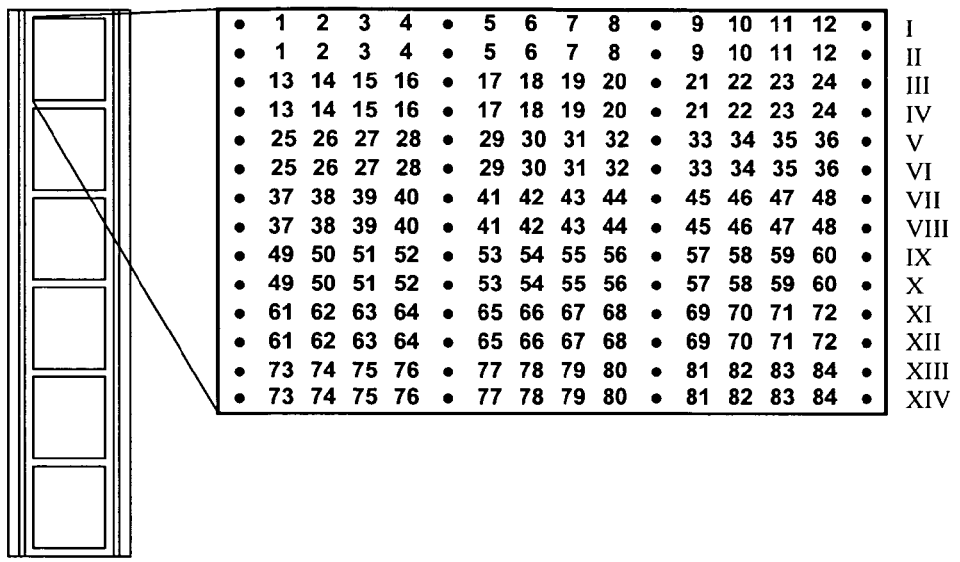

Fig. 1

Table 1

| Measurement area contents reference number | Solution applied to discrete measurement areas |
|---|---|
| 1 – 9 | Purified Akt (0 ng/ml, 1 ng/nl, 3 ng/ml, 10 ng/ml, 30 ng/ml, 100 ng/ml, 300 ng/ml, 1000 ng/ml, 3000 ng/ml) in spotting buffer, with 0.1 mg/ml BSA |
| 10 - 12 | Spotting buffer |
| 13 – 21 | Purified Akt (0 ng/ml, 1 ng/nl, 3 ng/ml, 10 ng/ml, 30 ng/ml, 100 ng/ml, 300 ng/ml, 1000 ng/ml, 3000 ng/ml) in spotting buffer, with 0.1 mg/ml rat serum |
| 22 - 24 | Spotting buffer |
| 25 - 31 | Solutions of rat heart tissue lysate with different total protein content (0.025 mg/ml, 0.050 mg/ml, 0.1 mg/ml, 0.2 mg/ml, 0.3 mg/ml, 0.4 mg/ml, 0.5 mg/ml) in spotting buffer |
| 32 - 36 | Spotting buffer |

| 37 - 43 | Solutions of rat heart tissue lysate with different total protein content (0.025 mg/ml, 0.050 mg/ml, 0.1 mg/ml, 0.2 mg/ml, 0.3 mg/ml, 0.4 mg/ml, 0.5 mg/ml) in spotting buffer, with additionally in each case 1000 ng/ml purified Akt |
| --- | --- |
| 44 – 48 | Spotting buffer |
| 49 - 55 | Akt-free solution of rat serum with different total protein content (0.025 mg/ml, 0.050 mg/ml, 0.1 mg/ml, 0.2 mg/ml, 0.3 mg/ml, 0.4 mg/ml, 0.5 mg/ml) in spotting buffer |
| 56 – 60 | Spotting buffer |
| 61 – 67 | Serial dilution of rat serum in spotting buffer with additionally added, purified Akt (total protein concentration, Akt content: 0.025 mg/ml, 50 ng/ml; 0.050 mg/ml, 100 ng/ml; 0.1 mg/ml, 200 ng/ml; 0.2 mg/ml, 400 ng/ml; 0.3 mg/ml, 600 ng/ml; 0.4 mg/ml, 800 ng/ml; 0.5 mg/ml, 1000 ng/ml). |
| 68 – 72 | Spotting buffer |
| 73 – 81 | Solutions of rat heart tissue lysate in spotting buffer (0.3 mg/ml), with different concentrations of purified Akt (0 ng/ml; 0.91 ng/ml; 2.74 ng/ml; 8.2 ng/ml; 27.2 ng/ml; 74.0 ng/ml; 222 ng/ml; 667 ng/ml; 2000 ng/ml). |
| 82 – 84 | Spotting buffer |
| ● | Cy5-BSA (0.5 nM) in spotting buffer |

Table 1 (continued)

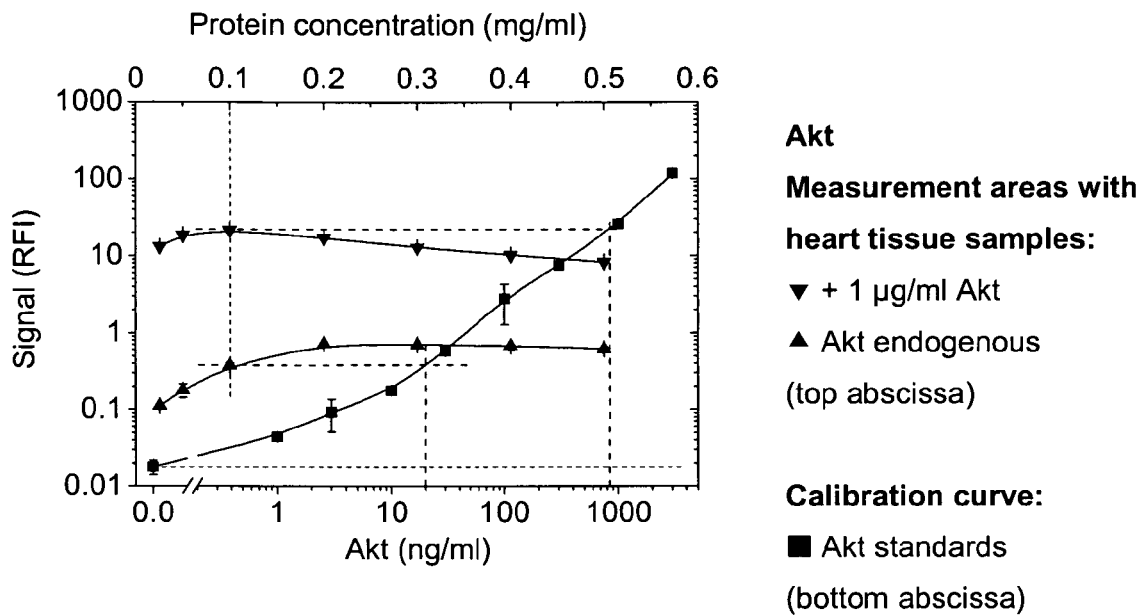

Akt
Measurement areas with heart tissue samples:
▼ + 1 µg/ml Akt
▲ Akt endogenous
(top abscissa)

Calibration curve:
■ Akt standards
(bottom abscissa)

Fig. 4

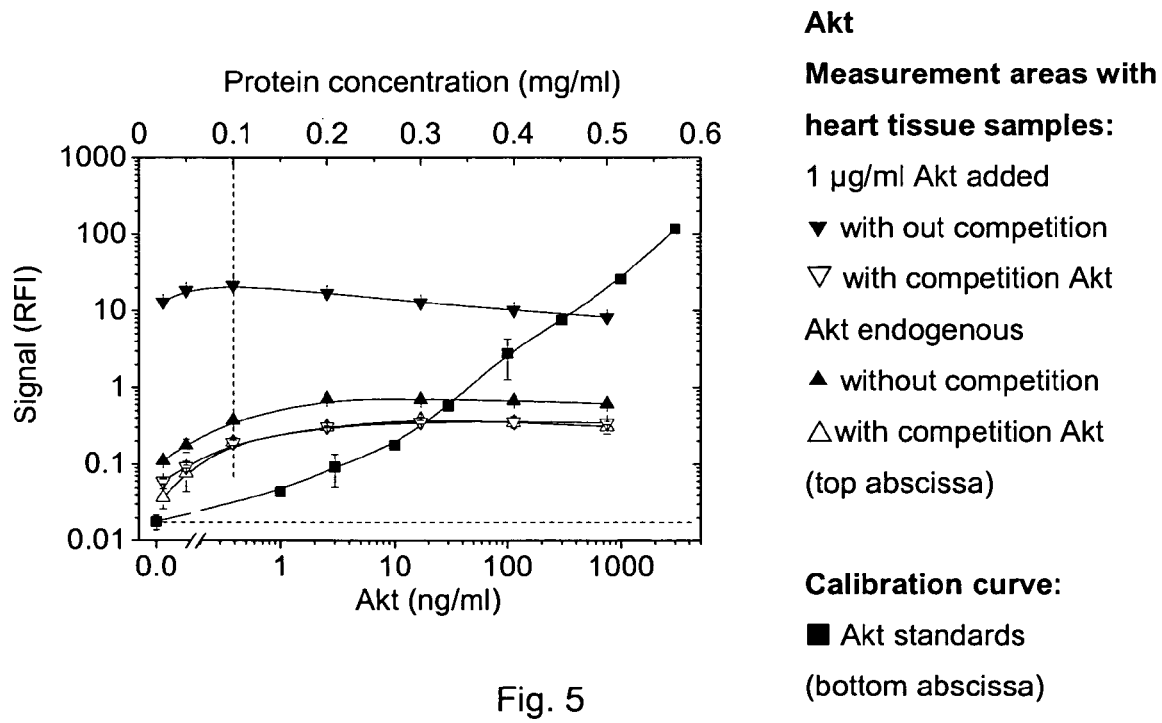

Akt
Measurement areas with heart tissue samples:
1 µg/ml Akt added
▼ with out competition
▽ with competition Akt
Akt endogenous
▲ without competition
△ with competition Akt
(top abscissa)

Calibration curve:
■ Akt standards
(bottom abscissa)

Fig. 5

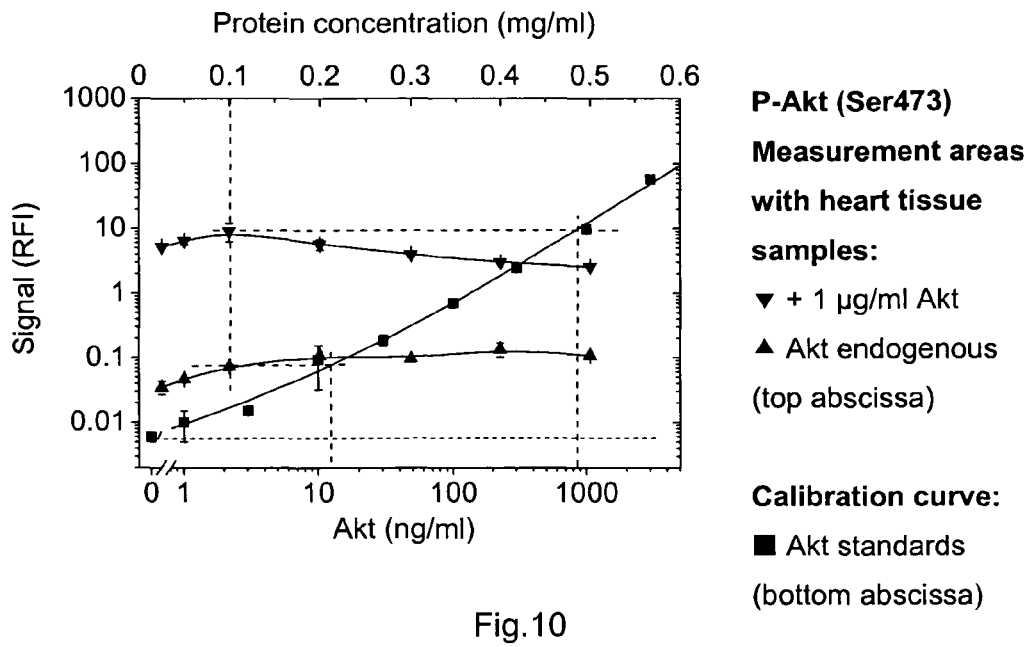

**P-Akt (Ser473)
Measurement areas
with heart tissue
samples:**

▼ + 1 µg/ml Akt
▲ Akt endogenous
(top abscissa)

Calibration curve:
■ Akt standards
(bottom abscissa)

Fig.10

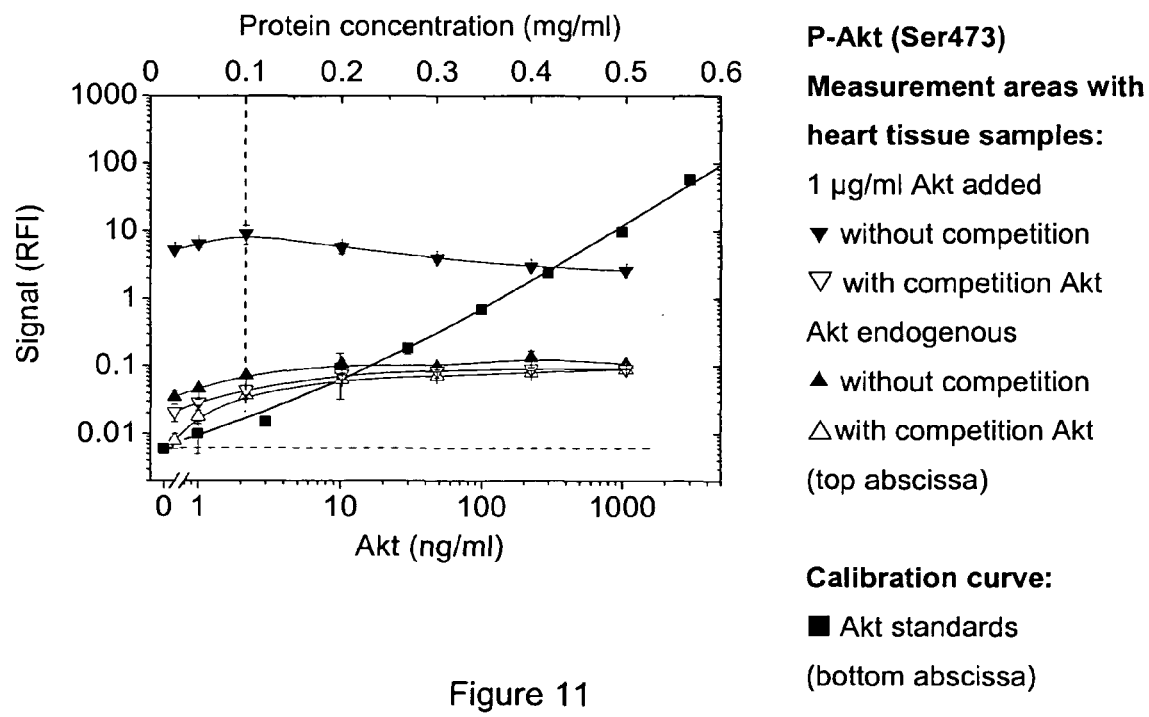

**P-Akt (Ser473)
Measurement areas with
heart tissue samples:**

1 µg/ml Akt added
▼ without competition
▽ with competition Akt
Akt endogenous
▲ without competition
△ with competition Akt
(top abscissa)

Calibration curve:
■ Akt standards
(bottom abscissa)

Figure 11

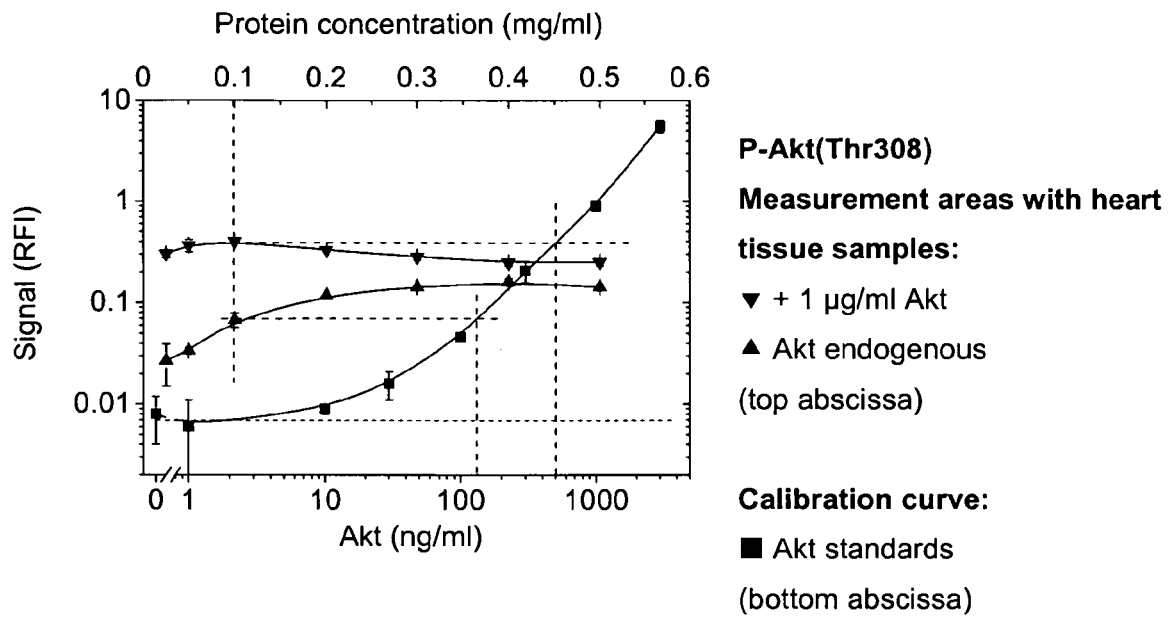

P-Akt(Thr308)
Measurement areas with heart tissue samples:

▼ + 1 µg/ml Akt
▲ Akt endogenous
(top abscissa)

Calibration curve:
■ Akt standards
(bottom abscissa)

Fig. 16

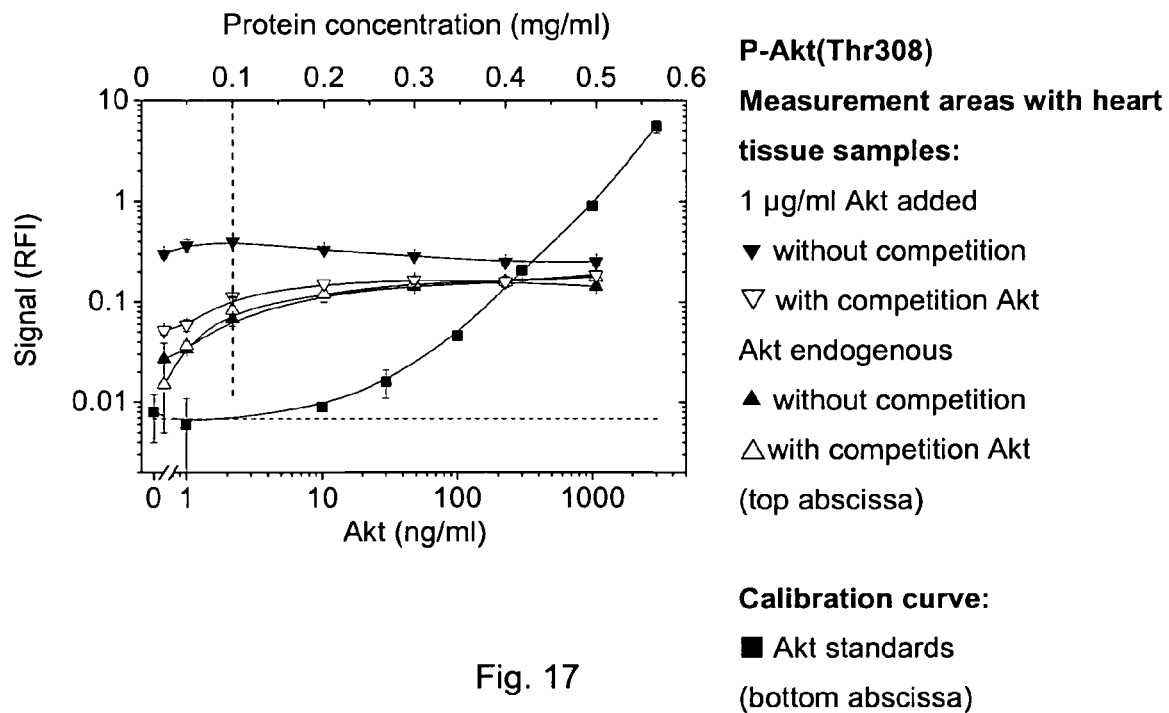

P-Akt(Thr308)
Measurement areas with heart tissue samples:
1 µg/ml Akt added
▼ without competition
▽ with competition Akt
Akt endogenous
▲ without competition
△ with competition Akt
(top abscissa)

Calibration curve:
■ Akt standards
(bottom abscissa)

Fig. 17

PROCESS FOR DETERMINING ONE OR MORE ANALYTES IN SAMPLES OF BIOLOGICAL ORIGIN HAVING COMPLEX COMPOSITION, AND USE THEREOF

This application is a U.S. national stage of International Application No. PCT/EP2005/011607 filed Oct. 29, 2005.

The present invention relates to a process for detecting one or more analytes in one or more samples of biological origin and complex composition

BACKGROUND OF THE INVENTION

Numerous fields of application require determining a multiplicity of biologically relevant analytes in a complex sample, for example in diagnostic processes for determining the state of health of an individual or the effect of a therapeutic treatment or in pharmaceutical research and development for determining the influence of biological systems such as, for example, an organism and the complex mode of action thereof by external actions such as, for example, by means of supplying biologically active compounds.

While known analytical separation methods are usually optimized in order to fractionate a very large number of compounds present in a given sample according to a pre-defined physicochemical parameter such as, for example, the molecular weight or the quotient of molecular charge and mass, in as short a time as possible, bioaffinity assays are based on using in each case one biological or biochemical or synthetic recognition element of very high specificity, in order to recognize and bind the corresponding (individual) analyte in a sample of complex composition in a highly selective manner. Detection of a multiplicity of different compounds thus requires the use of a corresponding number of different specific recognition elements.

An assay based on bioaffinity reactions may be carried out both in a homogeneous solution and on the surface of a solid support. Depending on the specific design of the process, the latter requires, after binding of the analytes to the corresponding recognition elements and, where appropriate, further detection substances and also, where appropriate, between various process steps, in each case washing steps in order to separate the produced complexes of said recognition elements and the analytes to be detected and also, where appropriate, further detection substances from the rest of the sample and the optionally employed additional reagents.

Processes for simultaneously detecting a multiplicity of different nucleic acids in a sample with the aid of corresponding complementary nucleic acids immobilized on a solid support in discrete, spatially separated measurement areas as recognition elements are now relatively widespread. For example, arrays of oligonucleotides as recognition elements, which are based on simple glass or microscope slides and which have a very high feature density (density of measurement areas on a shared solid support), have been disclosed. U.S. Pat. No. 5,445,934 (Affymax Technologies), for example, describes and claims arrays of oligonucleotides having a density of more than 1000 features per square centimeter.

Recently, descriptions of arrays and assays of a similar kind carried out therewith for simultaneously determining a multiplicity of proteins, for example in U.S. Pat. No. 6,365,418 B1, in particular using arrays of immobilized antibodies as recognition elements for the analytes to be detected, have become more frequent.

The patent documents regarding such "microarrays", for detecting both nucleic acids and other biopolymers such as, for example, proteins, describe in each case that a multiplicity of different specific recognition elements is immobilized in discrete measurement areas to generate an array for analyte recognition, and the sample to be studied containing the analytes (where appropriate in a complex mixture) is then contacted with this "capture array". According to the descriptions disclosed, different specific recognition elements are present here in each case in a form of the highest possible purity in different discrete measurement areas, and as a result usually different analytes of the sample bind to measurement areas with different recognition elements.

This type of known assay requires purifying and concentrating said specific recognition elements, to be immobilized in a form of the highest possible purity, by means of in parts very complicated steps. Since different recognition elements differ more or less greatly in their physicochemical properties (e.g. in their polarity), there are also corresponding differences in the conditions for optimal immobilization of said recognition elements, for example by adsorption or covalent binding, in discrete measurement areas on a shared solid support, where appropriate on an adhesion-promoting layer applied thereto. Consequently, the immobilization conditions chosen for immobilizing a multiplicity of different recognition elements (such as, for example, type of adhesion-promoting layer) can hardly be optimal for all recognition elements at the same time, but merely be a compromise between the immobilization properties of the various recognition elements. Another disadvantage is the fact that in each case only one supplied sample per array can be studied for analytes present therein in this kind of capture array.

There existed therefore the need for a modified assay design which enables a multiplicity of samples to be studied for analytes present in said samples, either simultaneously in one array or a plurality of arrays on a shared support or sequentially in a plurality of arrays on a plurality of supports. For this purpose it would be convenient to apply the samples to be studied themselves, rather than the different specific recognition elements, in discrete measurement areas in one or more arrays on one or more supports, either directly, i.e. in untreated form, or after as few preparation steps as possible. Such an assay design will be referred to hereinbelow as an "inverted assay architecture".

To satisfy this need, Paweletz et al. in Oncogene 2001, Vol. 20, 1981-1989, for example, have recently proposed such arrays for protein detection based on an inverted assay architecture under the name "reverse phase protein microarrays".

A common problem of such processes for analyte detection with the aid of microarrays as well as, in an even more general form, of assays which are carried out on surfaces and which are based on binding reagents binding specifically as specific binding partners to the analytes to be detected is the occurrence of unspecific binding events which are not based on the specific interaction between the analytes and the binding reagents and, where appropriate, further detection reagents used for their detection.

U.S. Pat. No. 5,726,064 describes various methods of compensating interferences of the assay signals by background signals such as, for example, background fluorescence, which may be caused in particular by unspecific binding events, and changes in temperature or pH, which could impair the assay signals observed. These methods are essentially based on providing additional areas designated to such compensation purposes, aside from the areas designated for generating the assay signals, on a shared solid support.

The US patent application 2004/0043508 A1 describes the extent of specific and unspecific binding to different surfaces for preparing capture arrays, which have been treated with different materials to minimize unspecific binding. In this context, coatings with electrostatic action are said to be advantageous for reducing unspecific binding.

U.S. Pat. No. 5,677,196 also describes different surface coatings for minimizing unspecific binding, in particular those comprising polyethylene glycols, and measurements of the absolute and relative proportions of unspecific binding, but again in a (sensor) format corresponding to capture arrays.

Said methods for minimizing the effects of unspecific binding on the assay results share the fact that they are based on altering the nature of the surface of the support, in order to prevent or minimize thereby binding of analytes or other binding and detection reagents used in the assay outside the measurement areas with analyte-specific recognition elements immobilized there. At the same time, it is tacitly assumed that unspecific binding does not occur in said measurement areas themselves; for such effects could not be taken into account with the aid of the processes described. In the case of capture arrays, with a well-defined composition of the compounds applied to the measurement areas, namely usually a standard form of recognition elements within a measurement area, the abovementioned requirement can be met substantially inter alia by carefully choosing said recognition elements and the binding and detection reagents used in the assay.

In the case of arrays for assays with an inverted assay architecture, i.e. with samples of biological origin and complex composition which are immobilized in the measurement areas, meeting the above requirement is difficult and hardly reliable, since the applied samples have an unknown composition with a multiplicity of different compounds of the biological sample matrix. Therefore it is to be expected that unspecific binding of binding reagents and optionally used detection reagents can occur to a significant extent even within the measurement areas.

It is the object of the present invention to provide, for such assays with arrays of measurement areas in which samples of biological origin and complex composition which contain analytes to be detected have been immobilized, a process which enables the proportion of signals emitting from the measurement areas that are optical signals generated by unspecific interaction with the added binding reagents and with the optionally added detection reagents to be determined.

Moreover, the present invention achieves the even more general object of determining the absolute amounts of one or more analytes in immobilized samples of biological origin and complex composition and of calibrating the signals being produced due to binding reagents binding to the analytes to be detected. Generating calibration curves for signals being produced from analytes present in supplied samples binding to their recognition elements immobilized in capture arrays by means of adding a suitable number of calibration solutions which contain the corresponding analytes in suitable concentrations is well known. Disadvantageously, this method requires the addition of a multiplicity of solutions to a corresponding multiplicity of arrays of measurement areas that are very similar to one another. The international applications, WO 01/092870 and WO 02/40998, propose that in one or more arrays in each case a plurality of measurement areas with biological or biochemical or synthetic recognition elements immobilized there at a different, controlled density are provided for detection of an analyte common to said measurement areas. Particular preference is given here to the fact that, with the binding signals between an analyte and its biological or biochemical or synthetic recognition elements being known to be a function of concentration and a sufficiently large "variation" of said recognition elements immobilized at a different controlled density in various measurement areas of an array, a calibration curve for said analyte may be generated even by means of adding a single calibration solution to said array. However, these different calibration methods for capture arrays always serve to calibrate the signals due to binding of the analytes present in an unknown concentration in solution to the immobilized recognition elements of the array. In contrast, for arrays with samples of biological origin and complex composition which are immobilized in discrete measurement areas, the problem is that of calibrating the analytes present in an unknown concentration in the immobilization matrix. This problem is solved by an array according to the invention of measurement areas and a quantitative assay of the invention based thereon. By way of combination with the abovementioned process of the invention for distinguishing proportions of signals generated by specific and unspecific binding, this enables absolute amounts and concentrations of analytes to be determined in a reliable manner.

Surprisingly, the invention allows the relative and/or absolute amount or relative and/or absolute concentration of analytes present in the immobilized samples of complex composition to be determined with high accuracy also for the kind of arrays used herein.

BRIEF DESCRIPTION OF THE FIGURES

FIG. 1: support with 6 arrays of measurement areas for the process of the invention. Grating structures for coupling light in and out are indicated to the left and right of the arrays. The enlarged detail depicts the geometric arrangement of the measurement areas in a single array. For the meaning of the measurement area contents reference numbers, see Table 1. Table 1 indicates the contents in each spot of the array shown.

FIG. 4: referenced fluorescence intensities for detecting endogenous Akt in samples prepared from rat heart tissue, with (top curve) and without (middle curve) additionally added purified Akt (1000 ng/ml), as a function of total protein concentration of the immobilization solutions (top abscissa). Also plotted is the calibration curve of FIG. 2 for detecting Akt, generated with measurement areas additionally containing 0.1 mg/ml BSA (as a function of the Akt concentration, bottom abscissa).

FIG. 5: referenced fluorescence intensities for detecting endogenous Akt in samples prepared from rat heart tissue, with (top curve) and without (middle curve) additionally added purified Akt (1000 ng/ml), as a function of total protein concentration of the immobilization solutions (top abscissa). Filled symbols: data obtained from measurement without competitor in the solution of the binding reagent ("anti-Akt" antibody, 5 nM); empty symbols: data obtained from measurement with 100 nM purified Akt as competitor in the solution of the binding reagent ("anti-Akt" antibody, 5 mM). Also plotted are the calibration curve of FIG. 2 for detecting Akt, generated with measurement areas additionally containing 0.1 mg/ml BSA (filled symbols; as function of the Akt concentration, bottom abscissa) and a corresponding calibration curve, generated with 100 nM Akt as competitor in the solution of the binding reagent (empty symbols; as function of the Akt concentration, bottom abscissa).

FIG. 10: referenced fluorescence intensities for detecting endogenous P-Akt (Ser473) in samples prepared from rat heart tissue, with (top curve) and without (middle curve) additionally added purified Akt (1000 ng/ml), as a function of total protein concentration of the immobilization solutions (top abscissa). Also plotted is the calibration curve of FIG. 7 for detecting P-Akt (Ser473), generated with measurement areas additionally containing 0.1 mg/ml BSA (as a function of the P-Akt (Ser473) concentration, bottom abscissa).

FIG. 11: referenced fluorescence intensities for detecting endogenous P-Akt (Ser473) in samples prepared from rat heart tissue, with (top curve) and without (middle curve) additionally added purified Akt (1000 ng/ml), as a function of total protein concentration of the immobilization solutions (top abscissa). Filled symbols: data obtained from measurement without competitor in the solution of the binding reagent ("anti-P-Akt (Ser473)" antibody, 5 nM); empty symbols: data obtained from measurement with 100 nM purified Akt as competitor in the solution of the binding reagent ("anti-P-Akt (Ser473)" antibody, 5 nM). Also plotted are the calibration curve of FIG. 7 for detecting P-Akt (Ser473), generated with measurement areas additionally containing 0.1 mg/ml BSA (filled symbols; as function of the P-Akt (Ser473) concentration, bottom abscissa) and a corresponding calibration curve, generated with 100 nM Akt as competitor in the solution of the binding reagent (empty symbols; as function of the Akt concentration, bottom abscissa).

FIG. 16: referenced fluorescence intensities for detecting endogenous P-Akt (Thr308) in samples prepared from rat heart tissue, with (top curve) and without (middle curve) additionally added purified Akt (1000 ng/ml), as a function of total protein concentration of the immobilization solutions (top abscissa). Also plotted is the calibration curve of FIG. 12 for detecting P-Akt (Thr308), generated with measurement areas additionally containing 0.1 mg/ml BSA (as a function of the assumed P-Akt (Thr308) concentration, bottom abscissa).

FIG. 17: referenced fluorescence intensities for detecting endogenous P-Akt (Thr308) in samples prepared from rat heart tissue, with (top curve) and without (middle curve) additionally added purified Akt (1000 ng/ml), as a function of total protein concentration of the immobilization solutions (top abscissa). Filled symbols: data obtained from measurement without competitor in the solution of the binding reagent ("anti-P-Akt (Thr308)" antibody, 5 nM); empty symbols: data obtained from measurement with 100 nM purified Akt as competitor in the solution of the binding reagent ("anti-P-Akt (Thr308)" antibody, 5 nM). Also plotted are the calibration curve of FIG. 14 for detecting P-Akt (Thr308), generated with measurement areas additionally containing 0.1 mg/ml BSA (filled symbols; as function of the assumed P-Akt (Thr308) concentration, bottom abscissa) and a corresponding calibration curve, generated with 100 nM Akt as competitor in the solution of the binding reagent (empty symbols; as function of the assumed P-Akt (Thr308) concentration, bottom abscissa).

DETAILED DESCRIPTION OF THE INVENTION

Figure 2:
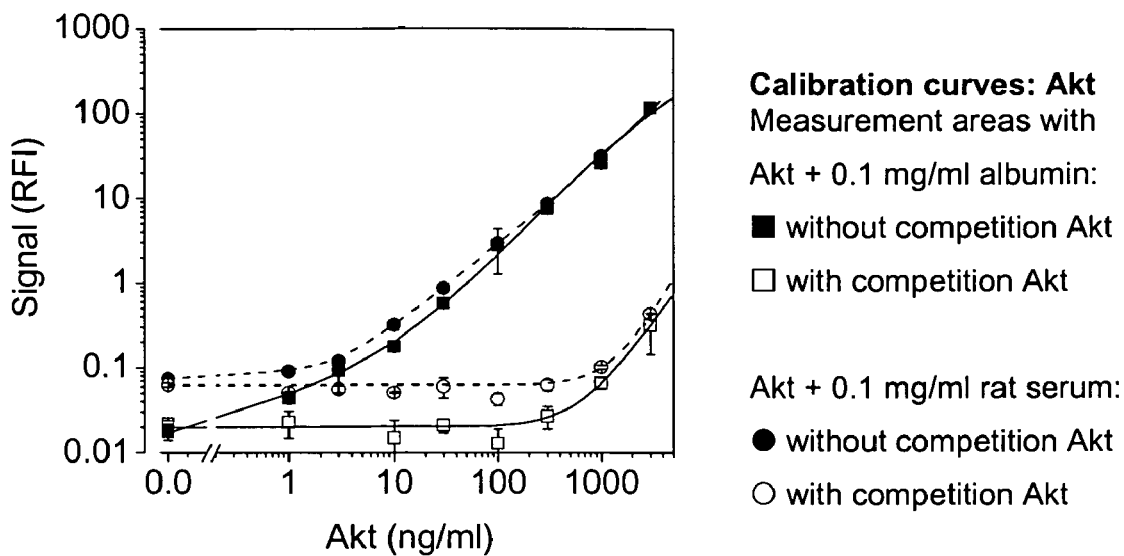
FIG. 2: referenced fluorescence intensities (RFI) from measurement areas with purified Akt applied thereto and with additional presence of 0.1 mg/ml BSA or 0.1 mg/ml rat serum in the immobilization solutions, as a function of the Akt concentration of the immobilization solutions. Filled symbols: calibration curves generated without competitor in the solution of the binding reagent ("anti-Akt" antibody, 5 nM), empty symbols: measurement curves generated with 100 nM Akt as competitor in the solution of the binding reagent.

In accordance with the present invention, spatially separated or discrete measurement areas on a solid support shall be defined by the closed area that is occupied by samples of biological origin and complex composition applied there or applied referencing reagents (such as, for example, fluorescently labeled albumin) or calibration reagents or applied mixtures thereof. Said areas may have any geometry, for example may be circular, rectangular, triangular, elliptical, etc.

The present invention firstly relates to a process for detecting one or more analytes in one or more samples of biological origin and complex composition, comprising the following steps:
(1) providing one or more samples of biological origin and complex composition,
(2) providing at least one solid support,
(3) applying small amounts of said samples of biological origin and complex composition, in diluted or undiluted form, to discrete sites either directly on said solid support or, after previous application of an adhesion-promoting layer, to said adhesion-promoting layer on the solid support, thereby generating one or more arrays of discrete measurement areas on the at least one solid support,
(4) contacting at least one array of discrete measurement areas with a first solution comprising one or more binding reagents as specific binding partners for the analytes to be detected and present in discrete measurement areas in the applied samples of biological origin and complex composition, and, optionally if required, one or more detection reagents, it being possible for binding reagents and detection reagents to be applied simultaneously or sequentially,
(5) measuring in a space-resolved manner first optical signals emitting from discrete measurement areas of one or more arrays which have been contacted with the first solution in step (4),
(6) recording said first optical signals,
characterized in that the proportion of the first optical signals measured that are optical signals generated due to unspecific interaction with the binding reagents added and with the detection reagents optionally added is determined by carrying out the following further steps:
(7a) applying a second solution comprising, in addition to the one or more binding reagents and optionally one or more detection reagents of the first solution added in step (4), a known high concentration of compounds which are of the same kind as the analytes to be detected and present in samples of biological origin and complex composition, which samples have been applied to discrete measurement areas, as competitors to said analytes to be detected and present in samples of biological origin and complex composition, which samples have been applied to discrete measurement areas, for specific binding of said binding reagents and of optionally additionally added detection reagents, to one or more arrays of discrete measurement areas generated in step (3), and/or
(7b) applying a third solution comprising, in addition to said one or more binding reagents and optionally one or more detection reagents of the first solution added in step (4), a known high concentration of substances which are of a similar kind as substances present in the sample matrix of the samples applied in step (3), for the purpose of competing with the substances of the sample matrix, which are present in the samples of biological origin and complex composition which have been applied to discrete measurement areas, for unspecific binding of said binding reagents and of optionally additionally added detection reagents, to one or more arrays of discrete measurement areas generated in step (3),
(8) measuring in a space-resolved manner second and/or third optical signals emitting from discrete measurement areas of one or more arrays which have been contacted with the second solution in step (7a) and/or with the third solution in step (7b), (9) recording said second and/or third optical signals, and comparing said first and second and/or third optical signals.

In steps (7a) and (7b), the binding reagents and the substances added for competition and also the optional detection reagents may be added in each case in the form of the addition of a single solution of these three groups of components. However, in the case of the additional addition of detection reagents, preference is given to applying firstly second or third solutions of mixtures of the binding reagents and the substances used for competition, optionally followed by one or more washing steps and a subsequent separate substep of addition of said detection reagents.

The term "of the solid support" or "of a solid support" is intended hereinbelow to also include the meaning of "of the at least one solid support" or "of at least one solid support".

The terms "first solution", "second solution", "third solution" are intended to include also the meaning of "multiplicity of first solutions", "multiplicity of second solutions" and "multiplicity of third solutions", respectively, it being possible for the solutions within such a multiplicity of solutions to have in each case the same or a different composition.

The term "sample" is used hereinbelow also synonymously with "sample of biological origin and complex composition", unless stated otherwise. The term of a "sample" in the singular also includes the term of a "plurality of samples", unless stated otherwise.

Said samples of biological origin and complex composition may be selected from the group of samples which is formed by lysates of cell populations, cell extracts, body fluids and components of body fluids, such as, for example, blood, serum, plasma, synovial fluid, tears, urine, saliva, tissue fluid and lymph, said samples being fractionated or non-fractionated samples.

Said samples may be obtained from healthy and/or diseased and/or stimulated and/or untreated cells from the group comprising human, animal, bacterial and plant cells. More specifically, said samples of biological origin and complex composition may be obtained from animal or human tissue such as, for example, organ, skin, hair, muscle, fat or bone tissue.

Different samples may have been obtained from the same organism or the same cell culture. It is then possible, by analyzing a plurality of measurement areas containing material from the same (or a very similar) organism or the same cell culture (or very similar cell cultures), for example, to obtain statistical information on the reproducibility of the relative molecular composition of the applied samples, determined in said measurement areas.

Different samples may in particular be obtained from various positions of the same organism. It is then possible, from the analyses on the corresponding discrete measurement areas, to obtain, for example, information on inhomogeneities of the relative molecular composition of the analytes to be detected in said organism from which said samples have been obtained. Such a procedure is very important, for example for examining organisms affected with cancer.

However, different samples may also be obtained from various organisms or various cell cultures. They may be, for example, samples from untreated organisms or organisms treated with a pharmaceutical drug. It is then possible, in a manner similar to an expression analysis in nucleic acid analysis, to study the influence of the particular drug on the relative molecular composition of the samples, i.e. in particular the composition of the multiplicity of compounds expressed by the cell populations from which they originate.

If cells are the starting material for the samples, they are typically lysed in a first preparation step. The lysates may be dissolved in a suitable solvent, for example a buffer solution and include known added admixtures, for example stabilizers such as protease inhibitors, in order to prevent biopolymers present from degrading. According to a preferred embodiment of the process of the invention, the lysates are prepared and processed in such a way that a sample obtained therefrom (i.e. samples of biological origin and complex composition) comprises the entire proteome of cell lines, cell cultures or cell tissues.

An important field of application of the process of the invention is the study of samples which comprise cell lysates or have been prepared from cell lysates for cellular expression of analytes (i.e. in particular protein expression) under different conditions. Depending on the aim of the particular study, the samples to be applied to the measurement areas can be selected in different ways.

A possible variant is based on the use of lysates from cell populations which are independent of one another (i.e. cell lines or cell culture mixtures). In this context, those cell populations which have grown independently of one another or have been cultured independently of one another (such as, for example, "in vitro cell cultures") shall be referred to as "independent of one another". Consequently, this term shall include, for example, cell populations which originate from various humans, animals, plants or organisms in general and from various organs, furthermore cell populations which are derived from different sites within an organism or organ, such as, for example, cancerous and healthy tissue from one and the same organ. The term shall also comprise cell populations which have been obtained from the same organism or organ at various points in time and/or have been subjected after removal to different treatments, stimulations or other different influences of another kind in an in vitro cultivation process. It is then possible, with the aid of the process of the invention and with the aid of samples obtained from such cell populations which are independent of one another, to generate, for example, a differential expression profile in order to detect differences in cellular expression and/or activation of cellular signal transduction cascades, for example between different organisms, between healthy and diseased organisms of the same kind, between various organs, etc. Of particular interest here is the influence of treatment or stimulation of said cell populations on cellular expression. In this context, the terms "treatment" or "stimulation" mean the addition of chemical or biochemical compounds (reagents or drugs) to the cell populations in question as well as the effect of different external physical conditions, for example in the form of irradiation with light of the ultraviolet to infrared spectrum, the influence of heat, the influence of electromagnetic fields, etc.

The process of the invention is also suitable for studying the effects of less accurately definable internal or external influential factors such as stress, disease, ageing, type of nutrition, etc., on cellular expression and/or activation (see below).

Owing to the high accuracy of the measurement results achievable by the process of the invention, the latter is in particular also suitable for studying the development of cellular expression and/or activation (see below) under the abovementioned conditions over periods of, for example, minutes, hours, days, weeks, months or years.

Another possible variant is based on the use of different cell lysates generated by various cell subpopulations which in turn have been obtained from a common cell population. Various cell subpopulations may be generated, for example, by removal from a common cell population at various points in time. Various cell populations may also be generated by removal from a common cell population and subsequent treatment or stimulations by different reagents and/or culturing under different external conditions (e.g. for studying the influence of irradiation by UV light, of heat shock, etc).

Typical reagents used for the treatment of cell populations for the above and other possible variants for application of the process of the invention comprise pharmaceutically active compounds, cytokins, antigens for cell stimulation, cell death-inducing stimulators, hormones, etc.

Preference is given to applying samples of complex composition which have been obtained from cell populations whose expression is to be compared with the aid of the process of the invention, in each case to a shared array of measurement areas, in order to be able to then study said samples for the analytes to be detected that are present under conditions as uniform as possible.

A sample may comprise additions of known concentrations of compounds of the same kind (as standards) as the analytes to be detected, comparable to a "spiking" of samples in chromatography. Such additions may be used, for example, for calibration purposes. Moreover, the samples may comprise additions of compounds which are similar to the sample matrix but different from the analytes to be detected, such as, for example, albumins (e.g. bovine serum albumin (BSA)), immunoglobulins or diluted serum, which compounds may serve, for example, to adjust the surface density of immobilized analyte molecule within a measurement area in a controlled manner. Analytes present in the samples or their fractions or in the dilutions of said samples or fractions, i.e. in particular biopolymers such as, for example, nucleic acids or proteins, may be present in native form or denatured form, for example after treatment with urea or surfactants (e.g. SDS). If necessary, it is possible to remove in particular insoluble components of the source material or intermediate material, in the case of a plurality of preparation steps prior to providing the samples of biological origin and complex composition, by suitable measures, for example centrifugation in the case of lysates as intermediate material. Preferably, the starting materials for preparing a "sample of biological origin and complex composition" are not subjected to any pretreatment steps other than filtration and/or fractionation and/or dilution.

The analytes present in the samples or their fractions or in the dilutions of said samples or fractions, i.e. in particular biopolymers such as, for example, proteins, are preferably present in denatured form, for example after treatment with urea, with the epitopes of said analytes being as freely accessible as possible for binding of their particular detection substances, for example antibodies. This is made possible, for example, by destroying the tertiary or quaternary structure as a result of the treatment with urea. Moreover, denatured samples have the advantage that arrays generated therefrom are very stable and can be stored and archived for analyses to be carried out at a later time over relatively long periods (up to years).

Fractionated samples may be obtained using a separation method, for example from the group of separation methods which comprises precipitations, filtration, centrifugation, HPLC and micro HPLC ("High Pressure Liquid Chromatography") by means of the method of normal phase chromatography, reverse phase chromatography, ion exchanger chromatography and hydrophobic interaction chromatography (HIC), size exclusion chromatography, gel chromatography, electrophoresis, capillary electrophoresis, electrochromatography, and free flow electrophoresis.

More specifically, said samples of biological origin and complex composition may comprise depleted serum. "Depleted serum" refers to those samples obtained from serum from which ingredients such as albumins, immunoglobulins and apolipoproteins have been removed to a high degree, for example by means of affinity chromatography.

The material for a sample to be analyzed of biological origin and complex composition may have been obtained, for example, by means of a method of the group of removal methods comprising tissue sections, biopsy and laser capture microdissection.

The process of the invention enables even only small volumes and amounts of sample used to be analyzed with high accuracy. An amount of sample here means the total amount which is applied to a discrete measurement area. For example, the material of a sample to be applied to a measurement area may correspond to the material of less than 100 cells. It may even correspond to the material of less than 10 cells. It is moreover possible for the material of a sample to be analyzed of biological origin and complex composition, which material is applied to a measurement area, to have a volume of less than 100 nl, preferably of less than 1 nl.

The analytes which are to be detected in the samples of biological origin and complex composition which have been applied to discrete measurement areas may be compounds from the group comprising proteins and their posttranslationally modified protein forms such as, for example, phosphorylated, glycosylated, methylated and acetylated forms of proteins, in particular proteins involved and interacting in cellular signal transduction pathways, such as, for example, kinases, kinase substrates, receptors and binding proteins for peptides, hormones, cofactors, membrane receptors, channel receptors, T-cell receptors, and enzymes, and also proteins and their posttranslationally modified protein forms which are derived from different cell compartments, such as, for example, cytosolic proteins, nuclear proteins, membrane proteins, mitochondrial proteins, and extracellular proteins such as, for example, proteins secreted into body fluids, and in particular also proteins over- or under-expressed under the influence of cellular treatment or stimulation, and also artificially modified or expressed proteins such as, for example, functionalized proteins with additional binding sites (tag proteins such as, for example, histidine tag proteins), mono- or polyclonal antibodies and antibody fragments, peptides, peptide fragments generated from intact proteins, glycopeptides, lectins, fluorescent proteins (such as, for example, green fluorescent protein, GFP, and the like), avidin, streptavidin, biotin, biotinylated proteins and differently conjugated proteins, oligosaccharides and nucleic acids (for example DNA, RNA).

"Analyte" means within the scope of the present invention such a molecular species which is distinguished from other compounds present in a sample to be analyzed and bound with the aid of a binding reagent used for this as specific binding partner and, where appropriate, of an additionally used detected reagent. For example, if an appropriate binding reagent binds only to the phosphorylated form but not to the unphosphorylated form of a compound or species to be detected, then both forms of said compound or species represent, according to this definition, two different analytes. If an appropriate binding reagent recognizes and binds any compounds or species when they are phosphorylated, then accordingly the corresponding phosphorylated compounds or species represent together a single analyte under this condition. Binding reagents as specific binding partners of an analyte according to said definition may be selected, for example, in such a way that they recognize and bind to only the phosphorylated form or the glycosylated form (or correspondingly the non-phosphorylated or non-glycosylated form) of a compound to be detected. The activity of a biological signal pathway in a cell or an organism may be correlated to the proportion of phosphorylated, methylated, acetylated or glycosylated compounds (depending on the nature of the signal pathway) which control said signal pathway. The relative proportion of the phosphorylated, methylated, acetylated or glycosylated form of the total amount, i.e. the quotient of the amount of a compound in its phosphorylated, methylated, acetylated or glycosylated form and the total amount of said compound in phosphorylated and non-phosphorylated form or methylated and non-methylated form or acetylated and non-acetylated form or glycosylated and non-glycosylated form, in a sample is referred to hereinbelow as degree of phosphorylation or methylation or acetylation or glycosylation of said compound in said sample. Degree of phosphorylation, degree of methylation, degree of acetylation and degree of glycosylation may be combined under the generic term of degree of activation of a compound. However, the degree of activation of a compound may also refer to other chemically modified forms of a compound. The process of the invention is particularly suitable also for determining the degree of activation of expressed proteins.

Binding reagents as specific binding partners may also be selected in such a way that they bind to a compound to be detected only if the latter has a particular three-dimensional structure. For example, many antibodies recognize and bind to only special subregions (epitopes) of a substance to be detected having a special three-dimensional structure. Depending on the conformational state of the corresponding compound to be detected, said subregions (epitopes) may be accessible or obscure to binding of the corresponding binding reagent. However, the binding reagents may also be selected in such a way that they bind to regions of the compound to be detected whose accessibility is independent of the three-dimensional structure of said compound. Using appropriately selected binding reagents therefore enables the relative proportion of the total amount of a compound to be detected in a sample, which has a specific conformational state, to be determined.

With a suitable selection of the binding reagents used and, where appropriate, additional detection reagents, the process of the invention makes it possible that proteins which are to be detected as analytes in the samples of biological origin and complex composition, which have been applied to discrete measurement areas, are distinguished according to their presence in phosphorylated and/or glycosylated, and/or methylated and/or acetylated form in said applied samples of biological origin and complex composition, in the course of step (4) as claimed in claim 1 after binding of binding reagents contacted therewith as specific binding partners, and optionally of additional detection reactions, and detected separately as different analytes in accordance with the above definition in the detection step (5) as claimed in claim 1.

It is also possible that proteins which are to be detected as analytes in the samples of biological origin and complex composition, which have been applied to discrete measurement areas, are not distinguished according to their presence in phosphorylated and/or glycosylated, and/or methylated and/or acetylated form in said applied samples of biological origin and complex composition, in the course of step (4) as claimed in claim 1 after binding of binding reagents contacted therewith as specific binding partners, and optionally of additional detection reactions, and not detected separately as different analytes but together as a single analyte in the detection step (5) as claimed in claim 1.

The process of the invention enables the degree of activation (according to the above definition) of one or more analytes present in an applied sample of biological origin and complex composition (i.e. in particular of proteins present) to be determined. More specifically, said process can be used for determining the degree of phosphorylation and/or the degree of methylation and/or the degree of acetylation and/or the degree of glycosylation of one or more analytes (in particular proteins) present in an applied sample.

The binding reagents used as specific binding partners of the analytes to be detected and present in discrete measurement areas in the applied samples of biological origin and complex composition may be selected, for example, from the group of compounds which comprises proteins, for example mono- or polyclonal antibodies and antibody fragments, peptides, enzymes, enzyme inhibitors, kinase substrates, aptamers, synthetic peptide structures, glycopeptides, hormones, cofactors, oligosaccharides, lectins, antigens for antibodies or T-cell receptors, biotin, avidin, streptavidin, proteins functionalized with additional binding sites (tag proteins such as, for example, histidine tag proteins) and complex formation partners thereof as well as nucleic acids (for example DNA, RNA, oligonucleotides) and nucleic acid analogs (e.g. PNA) and their derivatives having artificial bases.

Detection reagents used may be selected from a first group which comprises polyclonal or monoclonal antibodies and antibody fragments, nucleic acids and nucleic acid derivatives and their derivatives having artificial bases, biotin, avidin, streptavidin and neutravidin. The detection reagents may also be selected from a second group which comprises mass labels, for example in the form of nanoparticles, beads or colloids, and luminescent labels, for example in the form of luminescent dyes or luminescent nanoparticles such as quantum dots with excitation and emission wavelengths of between 200 nm and 1000 nm said mass or luminescent labels being bound to the binding reagents or attaching or binding thereto or being bound to detection reagents of the abovementioned first group of detection reagents or binding or attaching in a specific way to said detection reagents of the first group of detection reagents or binding or attaching to the complexes between the analytes to be detected which are present in the samples of biological origin and complex composition which have been applied to discrete measurement areas, and binding reagents bound thereto as specific binding partners, are formed. The binding reagents may also comprise the function of the detection reagents.

The term "luminescence" in this application refers to the spontaneous emission of photons in the ultraviolet to infrared range after optical or nonoptical such as, for example, electrical or chemical or biochemical or thermal, excitation. Examples of terms included under the term "luminescence" are chemiluminescence, bioluminescence, electroluminescence and in particular fluorescence and phosphorescence.

In a preferred variant of the process of the invention, said binding reagents as specific binding partners and optional detection reagents of a first solution and/or
binding reagents as specific binding partners, compounds of the same kind as the analytes to be detected and present in samples of biological origin and complex composition, which samples have been applied to discrete measurement areas, and optional detection reagents of a second solution and/or
binding reagents as specific binding partners, substances which are of a similar kind as substances present in the sample matrix of the samples of biological origin and complex composition which have been applied in step (3) in discrete measurement areas, and comprise optional detection reagents of a third solution, are preincubated with one another in each case, and said first, second or third solution is then contacted in a single addition step with said arrays of measurement areas.

A possible variant of the process of the invention is characterized in that different analytes are detected in a shared array of measurement areas by adding distinguishable detection reagents to said array. Preference is given here to the number of different analytes to be detected being equal to the number of distinguishable detection reagents used. Particular preference is given to distinguishable detection reagents differing in the excitation wavelength and/or emission wavelength of a luminescence.

Another variant of the process of the invention is characterized by the fact that a multiplicity of different analytes in a multiplicity of arrays of discrete measurement areas are detected by adding different binding reagents as specific binding partners for determining different analytes on various arrays of discrete measurement areas and/or by adding distinguishable detection reagents to said arrays of measurement areas.

A further possible variant is characterized in that different binding reagents are applied as specific binding partners for different analytes to various arrays for each different analyte to be detected.

It is advantageous if arrays of measurement areas containing samples of biological origin and complex composition applied thereto comprise those measurement areas in which known concentrations of compounds which are of the same kind as the analytes to be detected have been added as standards to the applied material. Particular preference is given here to the fact that arrays of measurement areas comprise a number of those measurement areas in which different known concentrations of compounds which are of the same kind as the analytes to be detected have been added as standards to the applied material, the number of such measurement areas and the level of said different known concentrations being sufficient in order to generate, by means of a single step of adding a first solution containing binding reagents as specific binding partners and optionally likewise detection reagents according to step (4) as claimed in claim 1 of the process of the invention, and of subsequent steps (5) and (6) as claimed in claim 1, a calibration curve for determining unknown concentrations of said analytes to be detected in the array. Again, it is possible here for the binding reagents and the optional detection reagents according to step (4) of the process of the invention to be added in a single addition step or in separate substeps, where appropriate with washing steps carried out in between. The material to which here the standards for analyte determination have been added may comprise, for example, only the components of the buffer solution used, added compounds similar to the sample matrix, such as albumins (in particular bovine serum albumin), immunoglobulins or diluted serum.

Preference is given to the fact that a plurality of the same kind of arrays of measurement areas are arranged on a solid support, with identical positions of measurement areas in various arrays, with regard to arrangement in rows and columns, meaning that samples of the same kind have been applied there.

There are various possible embodiments of applying the various solutions, namely the first solution containing binding reagents and, where appropriate, additionally detection reagents, the second solution containing additionally compounds of the same kind as the analytes to be detected as competitors and a third solution containing added compounds present in the sample matrix of the samples applied to the measurement areas, to arrays of measurement areas which are arranged on a shared solid support.

A first, preferred possible embodiment is characterized in that a first solution according to step (4) is added and first optical signals from the measurement areas of this array are measured and recorded according to steps (5) and (6) as claimed in claim 1, and second and/or third solutions according to steps (7a) and (7b) are added and the signals emitted from the measurement areas of the arrays in question are subsequently measured and recorded according to steps (8) and (9) as claimed in claim 1, on various measurement area arrays of the same kind, with identical positions of measurement areas in various arrays, with regard to arrangement in rows and columns, meaning that samples of the same kind have been applied there.

However, it is also possible for the first, second and third solutions to be applied to the same array of measurement areas (or the same plurality of measurement areas) sequentially, in each case after a sufficient number of regeneration and washing steps have been carried out. "Regeneration" here means such an intermediate step in which the complexes formed between the analytes and their binding reagents and, where appropriate, additionally added detection reagents after addition of the first solution, respectively the second or third solution are dissociated by adding suitable complex-destroying reagents such as, for example, "chaotropic" reagents with a high salt content/high ionic strength and/or strongly acidic character for dissociating antigen-antibody complexes, or urea solutions for dissociating hybridized nucleic acid strands, so that the immobilized analyte molecules are before addition of a second respectively third solution, in each case again accessible to binding of binding reagents and, where appropriate, further detection reagents. This variant of the process of the invention, however, is preferably carried out only if a high degree (for example of more than 80%, preferably more than 90%) of regenerability is guaranteed.

The concentrations of compounds which are of the same kind as the analytes to be detected and present in samples of biological origin and complex composition applied in discrete measurement areas and which are used as competitors to the analytes to be detected and present in samples of biological origin and complex composition applied in discrete measurement areas for the specific binding of said binding reagents and, where appropriate, of additionally added detection reagents, which concentrations are to be used preferably in the second solution to be applied, depend on the surface concentrations of said analytes to be expected in the measurement areas and on the equilibrium constants of the binding reactions between said analytes and their binding and detection reagents, respectively. The binding reagents are typically in a hundred-fold to thousand-fold dilution of the stock solutions obtained from the supplier. In the case of antibodies, such stock solutions are available with a content of typically 0.5-1 mg/ml, corresponding to concentrations in the range from 1-10 µM. The detection reagents are used in a comparable concentration range, i.e. typically 1-10 nM, as are the binding reagents. In the case of competition experiments, the competitors (e.g. phosphorylated peptide epitopes) are used in an at least tenfold, better a hundred-fold excess over the concentrations of the binding reagents. The substances used as competitors for unspecific linkage which are of a similar kind as substances present in the sample matrix of the samples of biological origin and complex composition (for example albumins, immunoglobulins or diluted serum) are typically used with a total protein content of from 10 µg/ml to 500 µg/ml of these third solutions (according to step (7b) of the process of the invention).

The process of the invention enables the proportion of total signals measured in the measurement areas and generated due to specific binding and additional unspecific binding, which are caused by unspecific interaction or unspecific binding, to be determined in two ways.

In the first option, the proportion of the measured first optical signals according to claim 1 that are optical signals generated due to unspecific interaction with the added binding reagents and optionally with the added detection reagents is determined from the difference of the optical signals measured according to step (8), after addition of the second solution according to step (7a), and the optical signals measured according to step (5), after addition of the first solution according to step (4).

The second option is characterized in that the proportion of the measured first optical signals according to claim 1 that are optical signals generated due to unspecific interaction with the added binding reagents and optionally with the added detection reagents is determined from the difference of the optical signals measured according to step (8), after addition of the third solution according to step (7b), and the optical signals measured according to step (5), after addition of the first solution according to step (4).

In combination with the abovementioned, preferred embodiment of the process of the invention, according to which arrays of measurement areas comprise a number of those measurement areas in which different known concentrations of compounds which are of the same kind as the analytes to be detected have been added as standards to the applied material, the number of such measurement areas and the level of said different known concentrations being sufficient in order to generate, by means of a single step of adding a first solution containing binding reagents as specific binding partners and optionally likewise detection reagents according to step (4) as claimed in claim 1, and of subsequent steps (5) and (6) as claimed in claim 1, a calibration curve for determining unknown concentrations of said analytes to be detected in the array, the process of the invention enables the (relative and/or absolute) concentration or (relative and/or absolute) amount of an analyte in a sample of biological origin and complex composition which sample has been applied to a measurement area to be determined from the difference between the optical signal (i.e. the first optical signal measured) measured for said measurement area and the proportion of optical signal generated due to unspecific interaction with the added binding reagents and optionally with the added detection reagents and by comparing said difference with a calibration curve for the analyte in question.

Said process steps will be explained in more detail in exemplary embodiments.

Owing to its high sensitivity and high accuracy and reproducibility, in particular due to a multiplicity of referencing and calibration methods which are independent of one another and can be used simultaneously or alternatively, the process of the invention is moreover characterized by the fact that differences, preferably of less than 20%, particularly preferably of less than 10%, in the (relative and/or absolute) concentration or (relative and/or absolute) amount of an analyte in various samples of biological origin and complex composition, which have been applied to various measurement areas, can be determined.

Owing to the measurement results obtained varying only slightly, the process of the invention is also suitable for studying the time course of (i.e. the alterations in) the amounts or concentrations of analytes (to be detected in the samples of biological origin and complex composition) under the influence of the illness of a biological organism or a cell culture and/or the external effect on an organism or a cell culture, for example due to treatment or stimulation with a biologically active compound (drug) or due to external physical action such as, for example, irradiation with light of a wavelength of the ultraviolet to infrared spectrum, influence of radioactivity or due to a heat effect.

Another possible embodiment of the process of the invention is therefore characterized in that a sample and one or more comparative samples have been obtained from the same site of origin at different points in time and that alterations in the amounts or concentrations of one or more analytes present in said samples with time are determined. "The same site of origin" here means the same organism or an organism of the same kind or the same cell culture or cell culture of the same kind (in each case after a disease or influence of the same kind and different length). Preferably, the process of the invention enables changes in the concentration or amount of said analytes with time of less than 20%, preferably of less than 10%, to be detected.

The simplest form of immobilizing the samples of biological origin and complex composition to be studied on a solid support is physical adsorption, for example due to hydrophobic interactions with the surface of said solid support. However, the extent of these interactions can be greatly altered by the composition of the solutions to be applied during the further course of the process and their physicochemical properties such as, for example, polarity and ionic strength. Specifically in the case of the sequential addition of various reagents in a multistep assay, adhesion of the samples of complex composition or of their components to the surface may be insufficient after a purely adsorptive immobilization. Preference is therefore given to an adhesion-promoting layer being applied to the solid support in order to improve adhesion of the samples to be applied in discrete measurement areas, to which adhesion-promoting layer the samples are then applied.

The thickness of said adhesion-promoting layer is preferably less than 200 nm, particularly preferably less than 20 nm.

A multiplicity of materials are suitable for preparing the adhesion-promoting layer. For example, the adhesion-promoting layer may comprise compounds of the group comprising silanes, functionalized silanes, epoxides, functionalized, charged or polar polymers and "self-assembled passive or functionalized mono- and multilayers", thiols, alkyl phosphates and alkyl phosphonates, and multifunctional block copolymers such as, for example, poly(L)lysine/polyethylene glycols.

Advantageously, areas between the discrete measurement areas "are passivated" for minimizing unspecific binding of binding or detection reagents, i.e. that components which are "chemically neutral" toward said binding reagents and/or detection reagents, i.e. which do not bind them, are applied between the spatially separated measurement areas.

Said components that are "chemically neutral" toward, i.e. which do not bind, the binding reagents and/or detection reagents may be selected from the group of albumins, in particular bovine serum albumin and human serum album, casein, unspecific, polyclonal and monoclonal, exogenous antibodies and antibodies which are empirically unspecific for the analyte(s) to be detected (in particular for immunoassays), detergents—such as, for example, Tween 20—, fragmented natural and synthetic DNA which does not hybridize with polynucleotides to be analyzed, such as, for example, an extract of herring or salmon sperm (in particular for polynucleotide hybridization assays), and also uncharged but hydrophilic polymers such as, for example, polyethylene glycols or dextrans.

A multiplicity of known processes are suitable for applying the samples of biological origin and complex composition directly to the solid support or to an adhesion-promoting layer previously applied to said support, which processes can be selected, for example, from the group of processes comprising ink jet spotting, mechanical spotting by means of pin, pen or capillary, microcontact printing, fluidically contacting the measurement areas with said samples by supplying the latter in parallel or crossed microchannels, with exposure to pressure differences or to electric or electromagnetic potentials and photochemical and photolithographic immobilization processes.

The arrays of measurement areas are preferably one- or two-dimensional arrangements of discrete measurement areas. The achievable density of measurement areas within an array of measurement areas and number of measurement areas on a common solid support is determined substantially by the spatial resolution of the application method employed. An array typically comprises more than 50, preferably more than 500, particularly preferably more than 5000, measurement areas. Each measurement area here may contain an immobilized sample which is identical to or different from other measurement areas. The measurement areas of an array are arranged in a density of more than 10, preferably more than 100, particularly preferably more than 1000, measurement areas per square centimeter.

An advantageous embodiment of the process of the invention is characterized in that a multiplicity of arrays of measurement areas are arranged on the solid support. More specifically, at least 5, preferably at least 50, arrays of measurement areas may be arranged on said support. It is particularly advantageous if different arrays of measurement areas are arranged in different sample containers. For example, the international patent applications WO 01/13096 and WO 01/43875 describe the way in which a solid support designed as an evanescent field sensor platform as a baseplate can be combined with a suitable upper part for generating a suitable array of sample containers, in each case for receiving an array of measurement areas.

Preference is given to 2-2000, preferably 2-400, particularly preferably 2-100, sample containers being arranged on the common, continuous solid support.

Particular preference is given to the sample containers being arranged in a grid, i.e. a sequence of rows and/or columns, which is compatible with the grid of standard microtiter plates. An established industrial standard here is an arrangement of 8×12 wells whose centers are spaced at approx. 9 mm. Compatible herewith are smaller arrays containing, for example, 3, 6, 12, 24 and 48 sample containers, with identical spacing. It is also possible to combine a plurality of such smaller arrays of sample containers in such a way that, after their combining, they are spaced at a whole multiple of said spacing of approx. 9 mm.

For some time, plates having 384 and 1536 wells, as whole multiples of 96 wells, on the same base area with correspondingly reduced well spacing (approx. 4.5 mm and 2.25 mm, respectively) which shall likewise be referred to as standard microtiter plates have also been used. The arrangement of sample containers as part of the kit of the invention may also be adapted to said geometry.

By adapting the grid of the sample containers to these standards, it is possible to use a multiplicity of commercially introduced and available laboratory pipettors and laboratory robots for adding the first, second or third solutions.

Such embodiments of a solid support for the process of the invention make possible an experimental concept which may be referred to as "multidimensional": for example, various samples, for example from different organisms (e.g. corresponding to columns), may be applied to the rows and columns of an array in different dilutions (e.g. corresponding to rows). Different arrays of measurement areas containing immobilized samples, in different sample containers, may then be contacted with different first and/or second or third solutions containing binding reagents and, where appropriate, detection reagents for determining different immobilized analytes in different arrays. It is apparent that such a variant of a support can be used for carrying out a virtually unlimited number of different experiments.

A multiplicity of embodiments of a solid support are suitable for the process of the invention. Preference is given to the solid support on which the arrays of discrete measurement areas are generated being essentially planar. "Essentially planar" means that, apart from, for example, structures possibly generated on the surface facing the measurement areas, such as, for example, depressions or elevations for generating devices for sample containers, said surface has a microscopic unevenness of less than 100 micrometers per centimeter extension along any axis in the plane of its surface.

It is also advantageous for many applications, if the solid support is non porous. "Non porous" here means that said support does not have any continuous porous structures and its (microscopic) surface roughness is less than 1 μm. The surface roughness of the solid support is preferably less than 20 nm, particularly preferably less than 2 nm.

It is also desirable for many applications that the optical support is essentially optically transparent at least the wavelength of an excitation light or measurement light which is guided in the direction of measurement areas during the detection steps of the process of the invention.

An incident "excitation light" here means that said light is used as an energy source for a secondary emission (generically referred to as "emission light"), such as, for example, fluorescence or general luminescence or a Raman radiation, or, for example, for excitation of a surface plasmon in a metal layer, which can be measured using a suitable detector. An incident "measurement light" means that this light is likewise used for interaction with the support and/or with analytes or their binding partners to be detected thereon for the purpose of analyte detection, but that, for example, no spectral changes in said measurement light or in a secondary emission are to be investigated, but, for example, changes in the adjustment parameters (such as, for example, in the resonance angle for coupling into a thin-film waveguide by means of a grating structure, see below) or in the propagation parameters of said light (such as, for example, the phase difference between light portions which run through different optical pathways such as the measurement path of an interferometer and the reference path, without interacting with a sample) are measured.

"Essentially optical transparency" of a material, a layer or a solid support at a particular wavelength means that the travel path length of a light guided in said material or in said layer or in said support or in the (high-refractive index) wave-guiding layer of a support designed as optical waveguide is greater than 2 mm at the wavelength in question, if said travel path length is not limited by structures for changing the direction of propagation of said light. For example, the travel path length, for example of optically visible light, i.e. the distance on the path of said light in the corresponding material, until the light intensity is reduced to a value of 1/e of the original intensity when said light entered said material, may be in the order of magnitude of from several centimeters (e.g. in thin-film waveguides) up to meters or kilometers (in the case of light guides for optical signal transmission). In the case of a grating-waveguide structure based on a thin-film waveguide, the length of the propagation vector of a light guided within the wave-guiding layer may be restricted to a few micrometers by an outcoupling diffractive grating (designed in the wave-guiding layer, see below). However, this restriction of the travel path length is then due to structuring rather than the material properties of the structure. In accordance with the present invention, such a grating-waveguide structure shall be referred to as "essentially optically transparent" if the travel path length of the light outside the areas of the grating structures is more than 2 mm.

Preferably, the material of an adhesion-promoting layer optionally applied to the solid support is also essentially optically transparent at least at the wavelength of an incident excitation light or measurement light.

The material of the solid support preferably comprises a material of the group comprising silicates such as, for example, glass or quartz, ceramics, metal oxides, plastics, in particular thermoplastics such as, for example, polycarbonates, acrylates, polyacrylates, in particular polymethyl methacrylates, polystyrenes, cyclo-olefin polymers and cyclo-olefin copolymers and combinations thereof (mixtures and/or layered structures). Preference is given to said plastics being moldable, embossable injection-moldable and/or millable and—for applications using luminescence detection—having very low intrinsic fluorescence. Preference is given to said materials meeting the requirement of essentially optical transparency at least at the wavelength of an incident excitation light or measurement light.

Various applications of the process of the invention desire embodiments of the solid support which are characterized in that said support comprises a plurality of layers with different optical properties.

A special embodiment is characterized in that the solid support has a thin metal layer, preferably comprising gold, silver or aluminum. Frequently, preference is additionally given here to said support comprising a further intermediate layer having a refractive index of <1.5, for example of silicon dioxide or magnesium fluoride, which is in contact with said metal layer. For this group of embodiments of a support, preference is moreover given to the thickness of the metal layer and of the possible intermediate layer being selected in such a way that a surface plasmon can be excited at the wavelength of an incident excitation light and/or at the wavelength of a luminescence generated. The thickness of the metal layer is preferably between 10 nm and 1000 nm, particularly preferably between 30 nm and 200 nm.

Most applications of the process of the invention desire at least the layer of the solid support, which is in contact with the measurement areas either directly or via an adhesion-promoting layer, to be essentially optically transparent at least at the wavelength of an incident excitation light or measurement light.

The solid support may comprise components from the group comprising microscope slides, microtiter plates, nanotiter plates, filters (e.g. comprising paper), membranes (e.g. nitrocellulose membranes) and microstructured supports (e.g. honeycomb structures or perforated structures made of silicon). In a manner similar to the established microtiter plates (containing typically 96, 384 or 1536 sample containers), similarly structured arrangements of open sample containers, but with smaller dimensions (typically in the order of magnitude of micrometers instead of millimeters), are referred to here as nanotiter plates.

A particularly preferred embodiment of a solid support suitable for the process of the invention is characterized in that the solid support comprises an optical waveguide which is either continuous or divided into discrete wave-guiding regions and which comprises one or more layers.

For the one or more detection steps of the process of the invention, it is preferred that the excitation light or measurement light is guided from one or more polychromatic or monochromatic light sources to one or more measurement areas of one or more arrays of measurement areas and optical signals from said measurement areas and/or changes or differences in the optical signals emitting from said measurement areas are measured and recorded in a space-resolved manner.

The excitation light or measurement light has preferably a wavelength of between 200 nm and 1200 nm.

Preference is given to using light sources with a narrow emission spectrum. Particularly preferred light sources are laser diodes and lasers.

Preference is given to using for space-resolved signal detection a space-resolving detector which may be selected, for example, from the group comprising CCD cameras, CCD chips, photodiode arrays, avalanche diode arrays, multichannel plates and multichannel photomultipliers. Optical systems and their components that are suitable for the detection steps of the process of the invention and optical detection methods are described, for example, in the international applications WO 95/33197, WO 95/33198 and WO 96/35940 whose contents are hereby incorporated in their entirety as part of the present invention.

There are various options of generating signals for measurement for analyte detection, depending on the physical design of the solid support. A possible variant is characterized in that the changes or differences in optical signals, to be measured in a space-resolved manner, are based on local differences in the effective refractive index at the surface of the solid support, which faces the measurement areas, or within a distance of less than 1 μm from said surface of said solid support, which local differences are caused by binding reagents and/or detection reagents binding to analytes present in discrete measurement areas in the samples of biological origin and complex composition which have been applied there.

A subvariant of this embodiment of the process of the invention is characterized in that the changes or differences in optical signals, to be measured in a space-resolved manner, are based on local differences in the resonance conditions for generating a surface plasmon in a thin metal layer as part of said solid support.

The conditions for generating a surface plasmon resonance and for combination with luminescent measurements and also with wave-guiding structures have been described in the literature many times, for example in U.S. Pat. Nos. 5,478,755, 5,841,143, 5,006,716 and 4,649,280.

The resonance angle (with variation of the incident angle at constant wavelength of the incident light) and the resonance wavelength (with constant incident angle and variation of the incident excitation wavelength) are accessible for measurement in order to determine changes in resonance conditions. Accordingly, with constant wavelength of the incident light, said change in resonance conditions can be a measurable change in the resonance angle for an incident excitation light for generating a surface plasmon in a thin metal layer of the solid support. Correspondingly, said change in resonance conditions may also be a change in the resonance wavelength of an incident excitation light for generating a surface plasmon in a thin metal layer as part of the solid support, with the incident angle (which should be equal to the resonance angle at least at a wavelength of a spectrally variable incident light directed onto the support) in this case preferably being kept constant.

Particular preference is given to those variants of the process of the invention which are characterized in that the solid support comprises an optical thin-film waveguide having a first, essentially optically transparent layer (a) upon a second, essentially optically transparent layer (b), with layer (a) having a higher refractive index than layer (b) and being in contact with the measurement areas either directly or by mediation via an adhesion-promoting layer.

The second optically transparent layer (b) here may comprise a material of the group comprising silicates such as, for example, glass or quartz, ceramics, metal oxides, plastics, in particular thermoplastics such as, for example, polycarbonates, acrylates, polyacrylates, in particular polymethyl methacrylates, polystyrenes, cyclo-olefin polymers and cyclo-olefin copolymers and combinations thereof (mixtures and/or layered structures). Preference is again given here to said plastics being moldable, embossable, injection-moldable and/or millable and—for applications using luminescence detection—having very low intrinsic fluorescence. Moreover, preference is given to said materials meeting the requirement of essentially optical transparency at least at the wavelength of an incident excitation light or measurement light.

Preference is given to the refractive index of the first optically transparent layer (a) being greater than 1.8. Preference is also given to the first optically transparent layer (a) comprising a material of the group of silicon nitride, $TiO_2$, ZnO, $Nb_2O_5$, $Ta_2O_5$, $HfO_2$, and $ZrO_2$, particularly preferably of $TiO_2$, $Ta_2O_5$ or $Nb_2O_5$.

Embodiments of (thin-) film waveguides suitable as solid support for the process of the invention are described, for example, in the international patent applications WO 95/33197, WO 95/33198 and WO96/35940.

For embodiments of the process of the invention having a solid support which comprises an optical waveguide, it is preferred that the excitation light or measurement light from one or more light sources is coupled into a wave-guiding layer of the solid support through one or more optical coupling elements which are selected from the group of prism couplers, evanescent couplers with optical waveguides brought into contact with each other and having overlapping evanescent fields, end face couplers with focusing lenses, preferably cylindrical lenses, arranged in front of an end side of the wave-guiding layer, and grating couplers.

Particular preference is given to said excitation light or measurement light being coupled into a wave-guiding layer of the solid support with the aid of one or more grating structures (c) which are developed in said wave-guiding layer as surface relief gratings having a certain grating period and grating depth.

It is also advantageous if light guided in a wave-guiding layer of the solid support is coupled out with the aid of one or more grating structures (c') which are designed in said wave-guiding layer and which have identical or different period and grating depth as grating structures (c).

Another variant of the process of the invention, which is based on refractive measurement methods, is characterized in that the changes or differences in optical signals, to be measured in a space-resolved manner, are based on local differences in the resonance conditions for coupling excitation light or measurement light of one or more light sources into a wave-guiding layer of the solid support by means of a grating structure developed in said wave-guiding layer.

In a manner similar to determining changes in resonance conditions for generating a surface plasmon resonance, the resonance angle (with variation of the incident angle at constant wavelength of the incident light) and the resonance wavelength (with constant incident angle and variation of the incident excitation wavelength) are accessible for measurement for determining changes in resonance conditions for coupling light into a wave-guiding layer via a grating designed therein. Accordingly, with a constant wavelength of the incident light, said change in resonance conditions may be a measurable change in the resonance angle for coupling light into a wave-guiding layer of the solid support. Correspondingly, said change in resonance conditions may also be a change in the resonance wavelength of an incident excitation light for coupling light into a wave-guiding layer of the solid support, with the incident angle (which should be equal to the resonance angle at least at a wavelength of a spectrally variable incident light directed onto the support) in this case preferably being kept constant.

The international patent application WO 01/88511 describes in detail various embodiments of grating-waveguide structures which are suitable for use as solid support for combination with the process of the invention. The detection methods described therein are also suitable for use in the detection step of the process of the invention for the above-described variant of using a refractive measurement method. Therefore, WO 01/88511 is hereby incorporated in its entirety as part of the present specification.

With respect to the technique of generating signals, preferred variants of the process of the invention are those which are characterized in that the changes or differences in optical signals, to be measured in a space-resolved manner, are based on local differences or changes in one or more luminescence events which are caused by binding reagents and/or detection reagents binding to analytes present in discrete measurement areas in the samples of biological origin and complex composition which have been applied there.

Particularly advantageous is the use of two or more luminescent labels having different emission wavelengths and/or different excitation spectra, preferably having different emission wavelengths and identical excitation wavelengths, for analyte detection. If a plurality of luminescent labels with different spectral properties, in particular different emission wavelengths, are bound to different binding and/or detection reagents which are contacted with the measurement areas, it is possible, for example, to determine different analytes within a single measurement area in a single detection step, i.e. contacting said measurement areas with said binding and/or detection reagents and simultaneously or subsequently detecting the luminescence events generated.

For example, such a variant of the process of the invention is particularly suitable for detecting at the same time, for example, the phosphorylated and non-phosphorylated form of a compound, in particular also within a single (common) measurement area, with the aid of two correspondingly different, for example directly labeled (e.g. with green- or red-emitting luminescent labels) binding reagents as specific binding partners.

In a similar manner it is also possible to detect within a single measurement area two or more different analytes at the same time, if two or more luminescent labels with different emission decay times are used for said analyte detection, and, with suitable excitation conditions (i.e. pulsed or modulated light excitation), resulting luminescence events are detected in a time-resolved manner which enables said luminescence events which decay with different speeds to be distinguished.

Advantageously, illumination with the excitation light is carried out in pulses lasting between 1 fsec and 10 minutes and the light emitting from the measurement areas is measured in a time-resolved manner.

A very particularly preferred embodiment of the process of the invention is characterized in that the solid support comprises an optical thin-film waveguide with a first layer (a) which is essentially optically transparent at least the wavelength of an incident excitation light upon a second layer (b) which is essentially optically transparent at least at the wavelength of an incident excitation light and which has a lower refractive index than layer (a), excitation light of a light source is coupled into the layer (a) by means of a grating structure (c) developed in said layer (a), said excitation light is guided as a guided wave to measurement areas which are located either directly on said layer (a) or by mediation via an adhesion-promoting layer on said layer (a), and luminescence events of compounds which are capable of luminescence and which are excited in the evanescent field of the light guided in said layer (a) to produce luminescence are measured in a space-resolved manner.

A particular variant here comprises determining changes in the effective refractive index on the measurement areas in addition to determining one or more luminescence events.

To improve the sensitivity further, it may be advantageous here, if the one or more luminescence events and/or determinations of light signals at the excitation wavelength are carried out in a polarization-selective manner. Preference is given here to measuring the one or more luminescence events with a polarization different from that of the excitation light.

The present invention further relates to a microarray for quantitative determination of one or more analytes in one or more samples of biological origin and complex composition, which microarray comprises a solid support, a first multiplicity of discrete measurement areas in which in each case small amounts of samples of biological origin and complex composition in diluted or undiluted form are immobilized either directly or by mediation via an adhesion-promoting layer, characterized in that at least a second multiplicity of measurement areas is provided in said array on the solid support, in which measurement areas substances of the same kind as the analytes to be detected are immobilized in different concentrations which are suitable, by means of contacting said microarray with a first solution comprising one or more binding reagents as specific binding partners for the analytes to be detected and present in the first multiplicity of discrete measurement areas in the applied samples of biological origin and complex composition, and for the substances of the same kind as said analytes to be detected, which are present in said second multiplicity of discrete measurement areas, and, optionally if required, one or more detection reagents, it being possible for binding reagents and detection reagents to be applied simultaneously or sequentially, and subsequent space-resolved measurement of first optical signals which are emitting from discrete measurement areas of one or more arrays, which have been contacted with the first solution, and recording said first optical signals, for generating a calibration curve for said analytes to be detected quantitatively and present in the immobilized samples of complex composition.

It may be advantageous that a third multiplicity of measurement areas is provided in said array on the solid support, in which in each case small amounts of samples of biological origin and complex composition in diluted or undiluted form and, in addition, known amounts added thereto of substances of the same kind as the analytes to be detected are immobilized. Said third multiplicity may be utilized, for example, for the control function of determining the degree of "recovery", as is the case also in the exemplary embodiments hereinbelow.

In a further development of the microarray of the invention, a fourth multiplicity of measurement areas is provided in said array on the solid support, in which substances are immobilized which are of a similar kind as substances present in the sample matrix of the samples applied to the first multiplicity of measurement areas.

It is preferred that the measurement areas of the second multiplicity of measurement areas also comprise substances which are of a similar kind as substances present in the sample matrix of the samples applied to the first multiplicity of measurement areas.

The substances which are of a similar kind as substances present in the sample matrix of the samples applied to the first multiplicity of measurement areas can be derived from the group comprising albumins, in particular bovine serum albumin, immunoglobulins, transferrins and fibrinogens.

It is moreover preferred that a fifth multiplicity of measurement areas is provided in said array on the solid support, which is used for referencing purposes. It is furthermore preferred that the measurement areas of the fifth multiplicity of measurement areas comprise substances which are selected from the group comprising mass labels, for example in the form of nanoparticles, beads or colloids, and luminescent labels, for example in the form of luminescent dyes or luminescent nanoparticles such as quantum dots with excitation and emission wavelengths of between 200 nm and 1000 nm.

Suitable for the microarray of the invention are any embodiments of solid supports and modifications thereof (for example by applying an adhesion-promoting layer), as described for the above-described process of the invention (for distinguishing the specific and unspecific binding portions of the observed signals). It is likewise possible to use any of the samples of complex composition, binding reagents, detection reagents and arrays of measurement areas described for said process of the invention in connection with a microarray of the invention.

The present invention further relates to a process for quantitative determination of one or more analytes in a sample of biological origin and complex composition, comprising the following steps:

providing one or more samples of biological origin and complex composition, providing a multiplicity of solutions of different concentrations of substances of the same kind as the analytes to be detected in the samples of complex composition, providing at least one solid support, generating a first multiplicity of discrete measurement areas as part of a microarray by applying small amounts of the samples of biological origin and complex composition in diluted or undiluted form to discrete sites, either directly on the solid support or, after prior application of an adhesion-promoting layer, on said adhesion-promoting layer on said solid support, generating a second multiplicity of discrete measurement areas as part of said microarray by applying in each case small amounts of the multiplicity of solutions of different concentrations of substances of the same kind as the analytes to be detected in the samples of complex composition, contacting the microarray with a first solution comprising one or more binding reagents as specific binding partners for the analytes to be detected and present in the first multiplicity of discrete measurement areas in the applied samples of biological origin and complex composition, and the substances of the same kind as said analytes to be detected, which substances are present in the second multiplicity of discrete measurement areas, and optionally if required, one or more detection reagents, it being possible for binding reagents and detection reagents to be applied simultaneously or sequentially, measuring in a space-resolved manner first optical signals emitting from said first and second multiplicities of discrete measurement areas of the microarray, recording said first optical signals from said first multiplicity of discrete measurement areas as signals characteristic for the latter contacting the first solution, recording the first optical signals from the second multiplicity of discrete measurement areas as signals characteristic for the latter contacting the first solution as a function of the concentration of the substances of the same kind as the analytes present in the samples of complex composition, which substances are present in said measurement areas, generating calibration curves for the analytes to be detected in the samples of complex composition from the recorded optical signals from the second multiplicity of discrete measurement areas, if required after prior subtraction of background signals and suitable referencing, quantitatively determining the analytes to be detected and present in the samples of complex composition by comparing the recorded first optical signals from the first multiplicity of discrete measurement areas with the calibration curves for the particular analytes, if required after previous subtraction of background signals and suitable referencing.

This process of the invention for quantitative determination of one or more analytes in a sample of biological origin and complex composition may be combined with the embodiments of the abovementioned process of the invention as claimed in claim 1 and its subclaims. Said combinations are likewise part of the present invention.

The invention moreover comprises the use of a microarray of the invention and/or of a process of the invention for quantitative determination of one or more analytes in a sample of biological origin and complex composition for quantitative and/or qualitative analyses for determining chemical, biochemical or biological analytes in processes of screening of drug libraries for efficiency determination in pharmaceutical research, combinatorial chemistry, clinical and preclinical development, for identifying, validating and monitoring biological or chemical marker substances ("biomarkers"), for identifying and verifying signal transduction pathways in proteomic research and systems biology, for affinity screening and in particular for antibody screening, for real time binding studies and for determining kinetic parameters in affinity screening and in research, for qualitative and quantitative analyte determinations, in particular for DNA and RNA analysis and determination of genomic or proteomic differences in the genome or proteome, such as, for example, single nucleotide polymorphisms, for measuring protein-DNA interactions, for determining control mechanisms for mRNA expression and for protein (bio)synthesis, for producing toxicity studies and for determining expression profiles, in particular for producing cellular expression profiles of diseased and healthy cell populations, with and without external stimulation, and comparison thereof, for studying the development of such expression profiles over time periods of minutes, hours, days, weeks, months or years, for determining biological and chemical marker substances such as mRNA, proteins, peptides or low molecular weight organic (messenger) substances, and also for detecting antibodies, antigens, pathogens or bacteria in pharmaceutical product research and development, human and veterinary diagnostics, agrochemical product research and development, symptomatic and presymptomatic plant diagnostics, stratification of patients in pharmaceutical product development and for therapeutic medicament selection, for detecting pathogens, harmful substances and pathogenic organisms, in particular salmonella, prions, viruses and bacteria, in particular in food analysis and environmental analysis.

Due to the high number of studies which can be carried out simultaneously on a common support under identical conditions, the process of the invention is particularly suitable for affinity screening, i.e. for comparing the affinities of various binding partners for a common specific binding partner, in particular of various antibodies for a common antigen.

Particular preference is also given to the use of the process of the invention for generating cellular expression profiles and comparison thereof. This relates in particular to the comparison of cellular expression profiles of diseased and healthy cell populations, with and without stimulation thereof. "Stimulation" here means both the addition of chemical or biochemical compounds to said cell populations and their treatment with different physical conditions such as, for example, irradiation, heat effect, etc. Owing to the high accuracy of the measurement results achievable by the process of the invention, the latter is specifically also suitable for studying the development of cellular expression under the abovementioned conditions over periods of, for example, minutes, hours, days, weeks, months or years.

The process of the invention is moreover particularly suitable for finding "biological or biochemical marker substances" of the abovementioned kind which are suitable for providing information about diseased cell populations in comparison with healthy cell populations, mutated or modified cell populations in comparison with wild-type cell populations, or about influencing cellular populations by stimulation or treatment thereof.

The microarray of the invention and the process of the invention are illustrated by way for example hereinbelow.

EXAMPLES

1. Analytes and Samples

In the following exemplary embodiment, the analytes to be detected are the marker protein "Akt" of the intracellular Akt signal pathway and two differently activated (phosphorylated) forms of this protein. Akt is a protein kinase and plays a key role in a multiplicity of physiological processes such as, for example, in glucose metabolism, cell growth, cell differentiation and programmed cell death (apoptosis). Akt is activated via phosphorylation of different amino acid side chains, inter alia serine 473 and threonine 308. Misregulation of said Akt signal pathway and inhibition of programmed cell death resulting therefrom play a decisive part in the onset of cancer, as a result of which this marker protein is of great therapeutic interest.

Analytical detection of Akt and its phosphorylated forms, P-Akt (Ser473) and P-Akt (Thr308), is carried out by means of different specific antibodies which bind either to the protein independently of its degree of phosphorylation or only to particular phosphorylated forms, for example only to P-Akt (Ser473) or only to P-Akt (Thr308). Thus it is possible by measuring a sample by means of applying three different antibodies to detect the overall Akt content and the particular content of its modified forms.

Detection of Akt and its phosphorylated forms is carried out in this exemplary embodiment in an unfiltered lysate of rat heart tissue which has been prepared in a highly denaturing lysis buffer containing urea and detergents and which contained the entire proteome of the cells present therein. Furthermore, rat serum containing no Akt was prepared in lysis buffer.

2. Supports Used in the Process of the Invention

The solid supports used for the process of the invention, in each case having the dimensions of 14 mm in width×57 mm in length×0.7 mm in thickness, are designed as thin-film waveguides, in each case comprising a glass substrate (AF 45) as essentially optically transparent layer (b) and a highly refractive layer of tantalum pentoxide of 150 nm in thickness applied thereto as essentially optically transparent layer (a). In said glass substrate, parallel to its length, two surface relief gratings (grating period: 318 nm, grating depth: (12+/−2) nm), spaced at 9 mm, are modulated. During subsequent application of said highly refractive layer, these structures which are to be used as diffractive gratings for coupling light into the highly refractive layer (a) are transferred to the surface of the tantalum pentoxide layer.

Such thin-film waveguides are particularly well-suited to the process of the invention, since they enable binding events close to the surface to be detected with a high ratio of measurement signal to background signal, making it possible to achieve deep detection limits. However, in principle any other embodiments of solid supports, as mentioned above, such as, for example, microscope slides or else microtiter plates, are also suitable for the process of the invention.

After carefully purifying the supports, a monolayer of mono-dodecyl phosphate (DDP) is generated on the surface of the metal oxide layer by spontaneous self-assembly as adhesion-promoting layer by means of deposition from an aqueous solution (0.5 mM DDP). Said surface modification of the previously hydrophilic metal oxide surface results in a hydrophobic surface (with a contact angle of about 100° with respect to water) on which the samples of biological origin and complex composition containing analytes as specific binding partners are to be applied for analyte detection in a specific binding reaction.

3. Reagents and Generation of Arrays of Measurement Areas

For competition experiments (see below) for determining signal portions caused by unspecific binding to the analytes, purified Akt (Pharmacia Italia Spa, Milan, Italy) is used as competitor in solution of the Akt to be detected and present in the immobilized samples of biological origin and complex composition ("endogenous Akt") as analyte. Said purified Akt is also used for generating calibration curves by means of addition in different immobilization solutions of different composition to be applied (see below).

The total protein concentrations of the stock solution for the samples (lysate of rat heart tissue in lysis buffer) from which the samples of biological origin and complex composition to be applied to the solid support are prepared, and of rat serum as a medium with a comparable composition to the sample matrix of the samples prepared from the rat heart tissue lysate are determined with the aid of a modified Bradford assay (PIERCE Coomassie Plus Kit (PIERCE # 23238) and are 17.3 mg/ml and 54.0 mg/ml, respectively.

Further dilution with a second buffer which likewise contains urea but is free of detergents ("spotting buffer") produces solutions of the rat heart tissue lysate with different total protein content (0.025 mg/ml, 0.050 mg/ml, 0.1 mg/ml, 0.2 mg/ml, 0.3 mg/ml, 0.4 mg/ml, 0.5 mg/ml) for application to individual measurement areas, without changing the protein composition of the diluted solutions compared to the stock solution. The solutions obtained of different total protein concentration represent samples of biological origin and complex composition to be studied (without other added supplements).

Moreover, solutions of the rat heart tissue lysate are prepared which have identical total protein concentrations (0.025 mg/ml, 0.050 mg/ml, 0.1 mg/ml, 0.2 mg/ml, 0.3 mg/ml, 0.4 mg/ml, 0.5 mg/ml) but additionally contain in each case 1000 ng/ml Akt. The measurement areas to be generated from these solutions are to be used for testing, whether analyte detection (of Akt or its phosphorylated forms) is independent of the total protein concentration in the particular measurement area.

Furthermore, in order to generate calibration curves of Akt and its phosphorylated forms, solutions of purified Akt (0 ng/ml, 1 ng/nl, 3 ng/ml, 10 ng/ml, 30 ng/ml, 100 ng/ml, 300 ng/ml, 1000 ng/ml, 3000 ng/ml) in spotting buffer are prepared, in each case with addition of 0.1 mg/ml bovine serum albumin (BSA). BSA here serves as a homogeneous and Akt-free sample matrix in which Akt is to be immobilized according to said different concentrations of the immobilization solutions on the support in discrete measurement areas.

In order to likewise generate calibration curves of Akt and the phosphorylated forms mentioned, albeit in a different sample matrix, solutions with the same purified Akt content (0 ng/ml, 1 ng/nl, 3 ng/ml, 10 ng/ml, 30 ng/ml, 100 ng/ml, 300 ng/ml, 1000 ng/ml, 3000 ng/ml) are prepared in spotting buffer, but with addition of 0.1 mg/ml rat serum instead of 0.1 mg/ml BSA. Rat serum here is used as a heterogeneous sample matrix which is similar to the rat heart tissue but is Akt-free and in which Akt is to be immobilized according to said different concentrations of the immobilization solutions on the support in discrete measurement areas.

In each case 6 identical microarrays of 224 measurement areas (spots) each, which in turn are in an arrangement of in each case 14 rows and 16 columns, are applied to the supports provided with the hydrophobic adhesion-promoting layer, using an inkjet spotter (GeSIM, Großerkmannsdorf, Germany). Each spot is generated by applying a single droplet of about 400 pl in volume to the surface of the support. In each case two identical measurement areas (two replicate spots) are generated per solution. Moreover, for negative controls, measurement areas containing spotting buffer but without any proteins as ingredients are also generated.

Apart from the abovementioned "sample spots", the microarrays also comprise in each case "reference spots": within each microarray, bovine serum albumin fluorescently labeled with Cy5 (Amersham) (Cy5-BSA, labeling rate: 3 Cy5 molecules per BSA molecule) is immobilized in part of the 224 measurement areas each. These measurement areas are used for referencing local differences in excitation light intensity within individual arrays and also between different arrays ("reference spots"). Cy5-BSA is applied to said measurement areas in each case in a concentration of 0.5 nM in urea-containing spotting buffer.

The geometric arrangement of the measurement areas in the in each case identical arrays is depicted in FIG. 1 and illustrated in Table 1.

After preparation of the arrays of measurement areas has been completed, the free, not protein-covered, hydrophobic surface areas of the supports are passivated by saturating them with bovine serum albumin (BSA), as a component which is "chemically neutral" toward, i.e. does not bind, binding reagents and/or detection reagents to be used, by incubating the surfaces with a BSA-containing buffer solution for 30 minutes. The supports with the measurement areas generated thereupon are washed with water (18 MΩ·cm) and finally dried in a nitrogen stream and stored at 4° C. until the detection process of the invention is carried out.

4. Design of Assays for Carrying Out the Process of the Invention

To further carry out the process of the invention, the supports provided with the arrays of measurement areas are in each case connected with an upper part for generating a linear arrangement of 6 sample containers (inner volume in each case: 15 µl) with the arrays of measurement areas arranged therein. Such arrangements of sample containers are described in the international applications WO 01/43875 and WO 02/103331 whose contents are hereby incorporated in their entirety as part of the present application.

The analyte detection step (according to step (4) of the process of the invention) is carried out in two substeps, in each of which one analyte per array of measurement areas is detected.

4.1. Use of Binding Reagents without Addition of Competitors

In a first substep, the arrays of measurement areas are incubated in the sample containers with a solution of a primary antibody as binding reagent ("anti-Akt" (# 9272) for detecting total Akt (without distinguishing between phosphorylated and non-phosphorylated forms), "anti-P-Akt (Ser473)" (#9271) for detecting phosphorylated P-Akt (Ser473), "anti-P-Akt (Thr308)" (#9275) for detecting phosphorylated P-Akt (Thr308) (all antibodies from Cell Signaling Technologies, Beverly, USA), in each case in a 500-fold dilution of the stock solution in assay buffer (corresponding to approx. 5 nM), at room temperature overnight.

After a washing step with in each case 200 µl of assay buffer to remove unbound binding reagents, the arrays of measurement areas are in the second substep in each case incubated with the detection reagent, namely fluorescently labeled Alexa Fluor 647 anti-rabbit Fab fragments (Molecular Probes; Eugene, USA), likewise in a 500-fold dilution of the stock solution in assay buffer, in the dark at room temperature for sixty minutes. The arrays of measurement areas are then again washed with in each case 200 µl of assay buffer in order to remove unbound detection reagents. The supports subjected to these process steps, connected with upper parts and buffer-filled sample containers generated in this way, are then stored until the detection step by means of excitation and detection of resulting fluorescence signals in a ZeptoREADER™ (see below).

4.2. Use of Binding Reagents with Addition of Akt as Competitor

Correspondingly, analyte detection is carried out in the presence of a competitor of the same kind as the analyte for specific binding to the binding reagents used and, where appropriate, additional detection reagents, likewise in two substeps of addition to the solid support with the arrays of measurement areas present thereon: firstly, the solutions of the binding reagents ("anti-Akt", "anti-P-Akt (Ser473)" or "anti-P-Akt (Thr308)", in each case approx. 5 nM) are preincubated in each case with an about twenty-fold excess of Akt (5 µg/ml corresponding to 100 nM). All antigen binding sites of the analyte-specific antibodies are expected here to be occupied by the corresponding competitor, as a result of which no specific binding sites of binding reagents are available any more for reaction with analyte molecules in the measurement areas. The Akt-containing solutions prepared in this way are then, in a manner similar to the first substep of 4.1., introduced into in each case another sample container with another but identical array of measurement areas like the array of measurement areas used under 4.1., and incubated therewith overnight, followed by a washing step, the subsequent substep of adding the detection reagent and the further substeps as described under 4.1. The procedure according to this section 4.2. corresponds to the substep (7a) of the process of the invention.

4.3. Use of Binding Reagents with Addition of Sample Matrix-Like Substances as Competitors In a manner similar to 4.1. and 4.2., analyte detection is carried out in the presence of substances additionally added to the binding reagents, which are identical or as similar as possible to substances present in the sample matrix and are used as competitors of the sample matrix components immobilized in the measurement areas for unspecific binding of the binding reagents. For this purpose, the solutions of the binding reagents ("anti-Akt", "anti-P-Akt (Ser473)" or "anti-P-Akt (Thr308)", in each case approx. 5 nM) are preincubated in each case with 0.1 mg/ml rat serum. The serum-containing solutions prepared in this way are then, in a manner similar to the first substep of 4.1., introduced into in each case another sample container with another but identical array of measurement areas like the array of measurement areas used under 4.1., and incubated therewith overnight, followed by a washing step, the subsequent substep of adding the detection reagent and the further substeps as described under 4.1. The procedure according to this section 4.3. corresponds to the substep (7b) of the process of the invention.

5. Excitation and Detection of Fluorescence Signals from the Arrays of Measurement Areas The fluorescence signals from the various arrays of measurement areas are measured sequentially and automatically using a ZeptoREADER™ (Zeptosens AG, CH-4108 Witterswil, Switzerland). This optical system has been described in more detail in the international patent application PCT/EP 01/10012 which is hereby incorporated in its entirety as part of this application.

6. Image Analysis and Referencing

The fluorescence signals from the measurement areas (spots) are determined with the aid of an image analysis software (ZeptoVIEW™, Pro 2.0 Release 2.0, Zeptosens AG, CH-4108 Witterswil), hereby determining average signal intensity and average local background signal intensity for each spot in its immediate environment. The background-corrected average net signal intensity is determined for each spot by subtracting the average local background signal from the average measured total signal intensity of the spot in question.

Referencing of the net signal intensity of all spots is carried out in each case with the aid of the Cy5-BSA reference spots. For this purpose, the net signal intensities of the "sample spots" are divided by the averaged signal intensity of the two closest neighboring "reference spots" within a row, which signal intensity is extrapolated to the position of the particular "sample spot". Said referencing offsets the local differences of the available excitation light intensity within each array of measurement areas and between different arrays.

Referenced net signal intensities of the spot duplicates (of in each case two identical measurement areas) are averaged last and are depicted in the corresponding figures as "RFI" data points (Referenced Fluorescence Intensity), with the error bars indicated corresponding to the particular standard deviations.

7. Carrying Out the Process of the Invention and Results

7.1. Determination of the Total Akt Content

7.1.1. Calibration Curves for Detecting Akt a) Use of Binding Reagents without Addition of Competitors In each case two segments of measurement areas are provided in the identical arrays of measurement areas for generating calibration curves of the kinase Akt (see FIG. 1):

segment 1: array rows I and II with measurement area contents numbers 1-9 with applied different concentrations (between 0 ng/ml and 3000 ng/ml) of purified Akt in spotting buffer additionally containing 0.1 mg/ml BSA, segment 2: array rows III and IV with measurement area contents numbers 13-21 with applied different concentrations (between 0 ng/ml and 3000 ng/ml) of purified Akt in spotting buffer additionally containing 0.1 mg/ml rat serum.

A solution of anti-Akt (5 nM) is added to a first sample container containing a first array of measurement areas. The further process substeps have previously been described under 4.1. The calibration curves of segment 1 of measurement areas (generated with solutions containing different concentrations of Akt and 0.1 mg/ml BSA added to the spotting buffer) (represented by filled squares) and of segment 2 of measurement areas (generated with solutions containing different concentrations of Akt and 0.1 mg/ml rat serum added to the spotting buffer) (represented by filled circles) are depicted in FIG. 2.

At concentrations of above 30 ng/ml Akt, the calibration curves of measurement areas with co-immobilized BSA and with co-immobilized rat serum are identical; at concentrations of below 30 ng/ml, the calibration curve of measurement areas with co-immobilized rat serum has higher signal values than that with co-immobilized BSA. The difference in signals is assigned to the contribution of unspecific binding of the binding reagent to the ingredients of the immobilized rat serum. When even higher concentrations of rat serum are added to the immobilization solution, the signal difference with measurement areas to whose generating immobilization solutions only BSA has been added is even more pronounced.

To determine the unknown Akt concentrations in the samples prepared from rat heart tissue, use is made of the calibration curves which were generated with the aid of immobilization solutions to which only BSA has been added, since said curves enable concentrations to be determined even at low Akt concentrations, below 30 ng/ml.

b) Use of Binding Reagents with Addition of Akt as Competitor

To test the proportion of signals due to unspecific binding to the calibration curves which have been established using the immobilization solutions with different sample matrix, a mixture of the solution of the "anti-Akt" antibody as binding reagent with an excess of Akt (5 µg/ml corresponding to a concentration of 100 nM) is introduced into a second sample container on another array with identical arrangement of the measurement areas as the array studied initially, and incubated with said measurement areas overnight, as described under 4.2. Under these conditions, the proportion of signals caused by specific binding of the antibody to immobilized Akt is expected to disappear completely, while the proportion of signals caused by unspecific binding remains.

As expected, complete suppression of the signal (caused by specific binding) is observed, within the accuracy of measurement, within the relevant concentration range for determining endogenous Akt, namely below 100 ng/ml (represented by empty symbols in FIG. 2)). The signals from measurement areas whose immobilization solutions contained rat serum (represented by empty circles) are higher than the signals of those measurement areas whose immobilization solutions contained, apart from the defined Akt concentrations, only BSA (represented by empty squares), according to the expected different proportions of unspecific binding to the sample matrix components. The signal increase observed with the highest Akt concentrations (1000 ng/ml and 3000 ng/ml in the immobilization solution) is attributed to the fact that the competitor concentration in solution under these conditions is apparently not sufficient in order to completely prevent specific binding of the binding reagent to immobilized Akt.

c) Use of Binding Reagents with Addition of Sample Matrix-Like Substances as Competitors To check the proportion of unspecific binding caused by the binding reagents binding to components of the sample matrix, rat serum with a total protein concentration of 0.1 mg/ml is added to the antibody solution. This solution is then introduced into a third sample container with a third array of again the same arrangement of measurement areas as the abovementioned first and second arrays, according to the procedure of section 4.3. Under these conditions, the proportions of signals generated by specific binding to immobilized Akt are expected to be retained, while the proportions of signals generated by unspecific binding to the sample matrix are expected to largely disappear.

Figure 3:
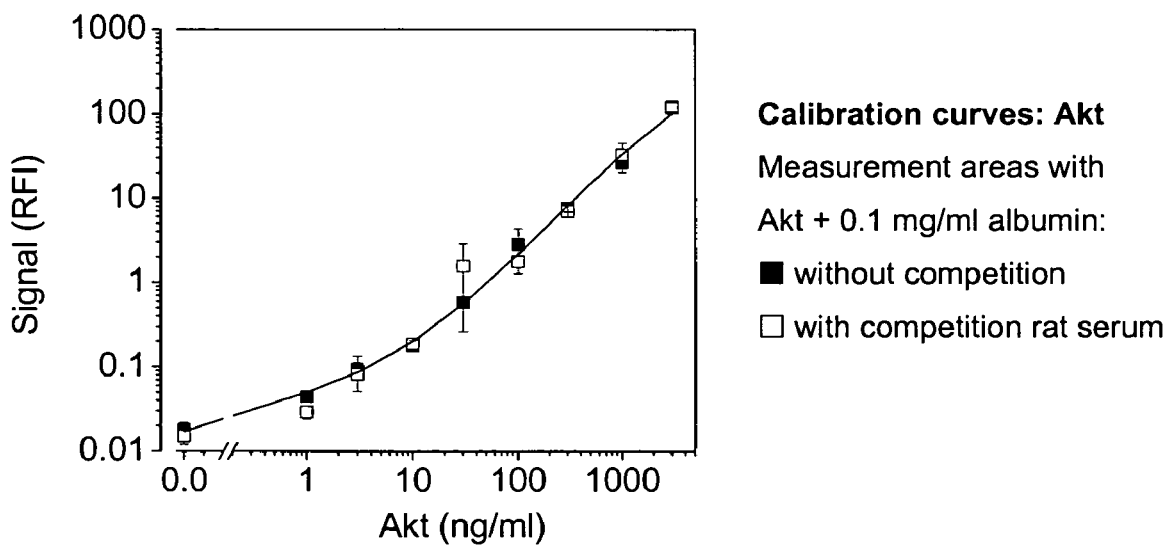
FIG. 3: referenced fluorescence intensities (RFI) from measurement areas with purified Akt applied thereto and with additional presence of 0.1 mg/ml BSA or 0.1 mg/ml rat serum in the immobilization solutions, as a function of the Akt concentration of the immobilization solutions. Filled symbols: calibration curves generated without competitor in the solution of the binding reagent ("anti-Akt" antibody, 5 nM), empty symbols: measurement curve generated with 0.1 mg/ml rat serum as competitor for unspecific binding in the solution of the binding reagent.

FIG. 3 depicts, by filled symbols, again the calibration curve described under section 7.1.1.a), generated using the first array without addition of competitors of the binding reagents. Deviations of the signals obtained using the third array by addition of the rat serum-containing solution of the antibody as binding reagent (represented by empty squares) from these calibration curves cannot be measured.

This suggests that, in the case of the "anti-total Akt" antibody, the generated calibration curve corresponds with high accuracy to the specific binding events and unspecific binding to the sample matrix takes place only to a very small extent.

7.1.2. Determination of the Total Akt Content in Samples Prepared from Rat Heart Tissue a) Use of Binding Reagents without Addition of Competitors Detection of the total Akt content in the samples of biological origin and complex composition prepared from rat heart tissue is carried out on the segment of measurement areas indicated by the measurement area contents numbers 25 to 31. The immobilization solutions generated for generating said measurement areas are from the same stock solution and were adjusted by dilution (see section 3.) to different total protein concentrations (between 0.025 mg/ml and 0.5 mg/ml).

The segment of measurement areas with the measurement area contents numbers 37 to 43 was generated by applying immobilization samples from an identical serial dilution of the stock solution from the rat heart tissue lysate, but with in each case purified Akt in a concentration of 1000 ng/ml being added to the immobilization samples. The signals to be measured with the aid of this segment are to be used for controlling, whether this high Akt concentration used (which is substantially higher than the expected natural, endogenous Akt content) is found again by comparing the fluorescence signals to be measured with the calibration curve (established using measurement areas with co-immobilized BSA), with identical total protein concentration (0.1 mg/ml).

The measurement is carried out, in combination with the part of the process of the invention that is described under 7.1.1.a, by means of adding a solution of "anti-Akt" (5 nM) to the first sample container containing the first array of measurement areas. The further process substeps have been described previously under 4.1.

FIG. 4 depicts the results (referenced fluorescence intensities). The fluorescence signals from measurement areas to which immobilization solutions prepared from rat heart tissue were applied are depicted as a function of the total protein concentration (FIG. 4, top abscissa), and the values of the referenced fluorescence signals of the calibration measurement with co-immobilized BSA (protein concentration: 0.1 mg/ml) are depicted as a function of the Akt concentrations of the immobilization solutions utilized for these measurement areas (FIG. 4, bottom abscissa).

The signals from the measurement areas without added Akt (i.e. with endogenous Akt naturally occurring in the immobilized samples), initially increase, as expected, with increasing protein concentration and reach a maximum valve, from a protein concentration of 0.2 mg/ml upward. No further signal increase is observed with further increasing protein concentration, similar to a saturation effect.

The signals from the measurement areas containing 1000 ng/ml added Akt (i.e. with endogenous Akt naturally occurring in the immobilized samples and additionally 1000 ng/ml purified Akt) correspondingly reach very high values. The Akt concentration of 1000 ng/ml added to the sample can be recovered and determined to (840±70) ng/ml by comparing the signal values with the simultaneously generated calibration curve with comparable total protein concentration (0.1 mg/ml, illustrated by the broken line at a protein concentration of 0.1 mg/ml, and by the broken line from the point of intersection of this line with the measured curve of signals from measurement areas with 1000 ng/ml added Akt in the direction of the calibration curve). The achieved recovery rate of 84% or precision of 8% is within the range of generally tolerated limits of 80%-120% recovery rate or more than 20% precision in an assay. This example thus demonstrates that the determination of analytes can be carried out with good assay accuracy and precision. The high recovery value likewise confirms that the measured curve generated on measurement areas with 0.1 mg/ml BSA added to the immobilization solutions (as protein matrix) is well-suited to calibrate the data of spots which were prepared from solutions containing rat heart tissue lysates.

A content of (20±2) ng/ml endogenous Akt is determined for the sample prepared from rat heart tissue with a protein content of 0.1 mg/ml by comparison with the calibration curve (illustrated by the broken line at a protein concentration of 0.1 mg/ml and by the broken line from the point of intersection of this line with the measurement curve of signals from measurement areas containing only endogenous Akt in the direction of the calibration curve).

b) Use of Binding Reagents with Addition of Akt as Competitor

To determine the proportion of signals due to unspecific binding to the measured curve from measurement areas which have been generated using the immobilization solutions based on rat heart tissue as sample matrix, a mixture of the solution of the "anti-Akt" antibody as binding reagent with an excess of Akt (5 µg/ml corresponding to a concentration of 100 nM) is introduced into a second sample container on another array with identical arrangement of the measurement areas as the array studied initially, and incubated with said measurement areas overnight, as described under 4.2. Under these conditions, the proportion of signals caused by specific binding of the antibody to immobilized Akt is expected to disappear completely, while the proportion of signals caused by unspecific binding remains.

FIG. 5 depicts the results of the competition experiment, together with the results of the corresponding measurements without the presence of a competitor in the solution of the binding reagent, described above under 7.1.2.a). Filled symbols indicate in each case the results without the presence of a competitor (measured on the first array), and empty symbols indicate the signals measured in the presence of the competitor (measured on the second array). The fluorescence signals from measurement areas whose immobilization solutions were prepared from rat heart tissue lysates (both from determining the naturally occurring endogenous Akt, without additionally added Akt, measurement area contents reference numbers 25 to 31, and with 1000 ng/ml additionally added, purified Akt, measurement area contents reference numbers 37 to 43, according to FIG. 1) are depicted as a function of the protein concentration of the immobilization solution (FIG. 5, top abscissa). The calibration curve, described in 7.1.1., for detecting Akt (with 0.1 mg/ml BSA in the immobilization solutions) is plotted as a function of the Akt concentration (FIG. 5, bottom abscissa).

In the presence of the competitor, the signals from the measurement areas for determining the endogenous Akt are distinctly reduced. The difference between the measured curves in the absence and in the presence of the competitor represents the proportion of signals caused by specific binding.

An even more distinct reduction of the referenced fluorescence signals is observed for the measurement areas whose immobilization solution additionally contained an excess of Akt (1000 ng/ml). The measured curves generated in the presence of 100 mM Akt as competitor in solution from the two segments of measurement areas (for determining endogenous Akt and for control measurement with 1000 ng/ml Akt in the immobilization solution) coincide exactly. The remaining signal (empty symbols) which increases up to a protein concentration of 0.3 mg/ml and then remains constant, corresponds to the signal contribution due to unspecific binding (to the proteins of the sample matrix), which contribution naturally increases with increasing surface concentration of the proteins, until the surface of the measurement areas is completely covered.

Figure 6:
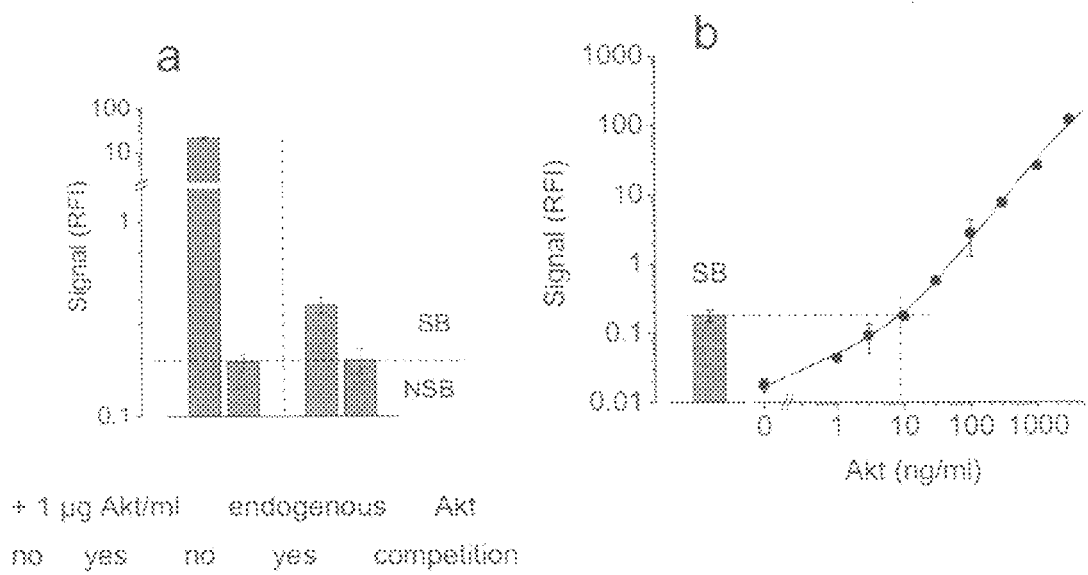
FIG. 6: determination of the proportions of the signals of FIG. 5 caused by specific binding at a protein concentration of 0.1 mg/ml from comparing the data in the presence and absence of the competitor in solution (FIG. 6*a*), and determination of the content of endogenous Akt from comparing the proportion of signal caused by specific biding ("SB") with the calibration curve (FIG. 62*b*).

FIG. 6 illustrates determination of the signal portions caused by specific binding at a protein concentration of 0.1 mg/ml from comparing the data in the absence and presence of the competitor in solution (FIG. 6a), and determination of the endogenous Akt content from comparing the signal portion caused by specific binding ("SB") with the calibration curve (FIG. 6b). The signal portions (0.20 RFI) caused by unspecific binding ("NSB") are of the same size for signals from measurement areas containing only endogenous Akt (0.373 RFI) and those containing additionally added 1000 ng/ml purified Akt (approx. 20 RFI), within the accuracy of measurement. A content of (8.8±1.3) ng/ml endogenous Akt is determined by comparing the difference between the total signal and the unspecifically caused signal with the calibration curve (FIG. 6b). Comparison with the determination of Akt in section 7.1.2.a), in which signal portions generated by unspecific binding were not discriminated, indicates that about 56% of the Akt content provisionally determined there must be assigned to the contribution of unspecific binding.

c) Use of Binding Reagents with Addition of Substances Similar to the Sample Matrix as Competitors To check the proportion of unspecific binding caused by the binding reagents binding to components of the sample matrix, rat serum with a total protein concentration of 0.1 mg/ml is added to the antibody solution. This solution is then introduced into a third sample container with a third array of again the same arrangement of measurement areas as the abovementioned first and second arrays, according to the procedure of section 4.3. Under these conditions, the proportions of signals generated by specific binding to immobilized Akt are expected to be retained, while the proportions of signals generated by unspecific binding to the sample matrix are expected to largely disappear.

Figure 7:
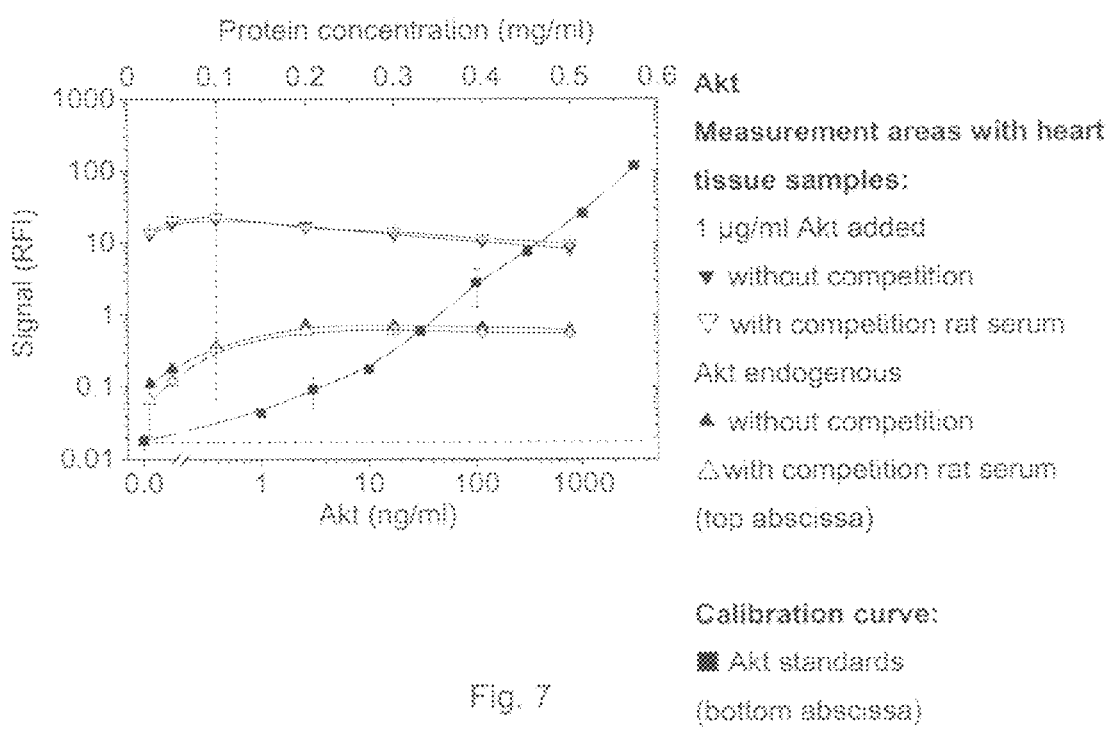
FIG. 7: referenced fluorescence intensities for detecting endogenous Akt in samples prepared from rat heart tissue, with (top curve) and without (middle curve) additionally added purified Akt (1000 ng/ml), as a function of total protein concentration of the immobilization solutions (top abscissa). Filled symbols: data obtained from measurement without competitor in the solution of the binding reagent ("anti-Akt" antibody, 5 nM); empty symbols: data obtained from measurement with 0.1 mg/ml rat serum as competitor for unspecific binding in the solution of the binding reagent ("anti-Akt" antibody, 5 mM). Also plotted are the calibration curve of FIG. 2 for detecting Akt, generated with measurement areas additionally containing 0.1 mg/ml BSA (filled symbols; as function of the Akt concentration, bottom abscissa) and a corresponding calibration curve, generated with 0.1 mg/ml rat serum as competitor for unspecific binding in the solution of the binding reagent (empty symbols; as function of the Akt concentration, bottom abscissa).

The results of the competition experiment with rat serum in solution are depicted in FIG. 7, together with the results of the corresponding measurements, described above under 7.1.2.a), without the presence of a competitor in the solution of the binding reagent. Filled symbols indicate in each case the results without the presence of a competitor (measured on the first array), and empty symbols indicate the signals measured in the presence of the competitor (measured on the third array). The fluorescence signals from measurement areas whose immobilization solutions were prepared from rat heart tissue lysates (both for determining the naturally occurring endogenous Akt, without additionally added Akt, measurement area contents reference numbers 25 to 31, and with 1000 ng/ml additionally added, Akt, measurement area contents reference numbers 37 to 43, according to FIG. 1) are depicted as a function of the protein concentration of the immobilization solution (FIG. 7, top abscissa). The calibration curve, described in 7.1.1., for detecting Akt (with 0.1 mg/ml BSA in the immobilization solutions) is plotted as a function of the Akt concentration (FIG. 7, bottom abscissa).

The presence of rat serum in solution as competitor for unspecific binding does not result in any significant shift of the measured curves; the referenced fluorescence signals measured in the presence and absence of rat serum are in each case identical, within the accuracy of measurement.

This suggests that, in the case of the "anti-total Akt" antibody there is no significant unspecific binding to the sample matrix.

7.2. Determination of the P-Akt (Ser473) Content

7.2.1. Calibration Curves for Detecting P-Akt (Ser473)

a) Use of Binding Reagents without Addition of Competitors

Calibration curves for determining the phosphorylated form, P-Akt (Ser473), are established by using segments of identical measurement areas, in the manner of the above-described determination of Akt.

Segment 1: array rows I and II with measurement area contents numbers 1-9 with applied different concentrations (between 0 ng/ml and 3000 ng/ml) of purified Akt in spotting buffer additionally containing 0.1 mg/ml BSA, segment 2: array rows III and IV with measurement area contents numbers 13-21 with applied different concentrations (between 0 ng/ml and 3000 ng/ml) of purified Akt in spotting buffer additionally containing 0.1 mg/ml rat serum.

The purified Akt is assumed to be completely phosphorylated, i.e. phosphorylated at Ser473 and at Thr308.

Figure 8:
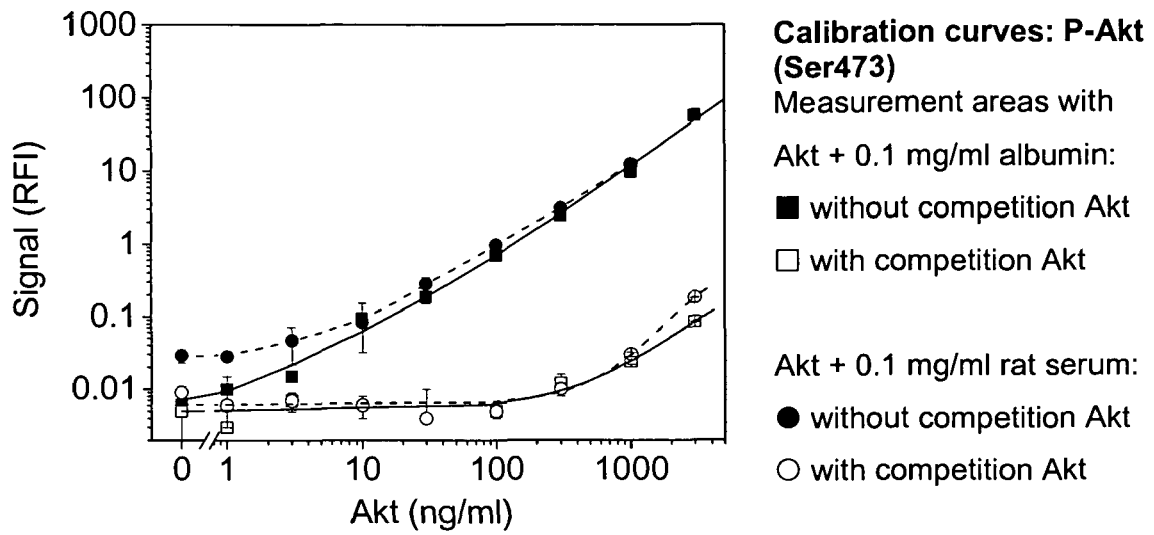
FIG. 8: referenced fluorescence intensities (RFI) from measurement areas with purified Akt applied thereto and with additional presence of 0.1 mg/ml BSA or 0.1 mg/ml rat serum in the immobilization solutions, as a function of the P-Akt (Ser473) concentration of the immobilization solutions. Filled symbols: calibration curves generated without competitor in the solution of the binding reagent ("anti-P-Akt (Ser473)" antibody, 5 nM), empty symbols: measurement curve generated with 100 nM Akt as competitor in the solution of the binding reagent.

A solution of anti-P-Akt (Ser473) (5 nM) is added to a fourth sample container containing a fourth array of measurement areas. The other process substeps have been described previously under 4.1. The calibration curves of segment 1 of measurement areas (generated using solutions containing different concentrations of Akt and 0.1 mg/ml BSA added to the spotting buffer) and of segment 2 of measurement areas (generated using solutions containing different Akt concentrations and 0.1 mg/ml rat serum added to the spotting buffer) are depicted in FIG. 8 (filled symbols).

At concentrations of above 10 ng/ml Akt, the calibration curves of measurement areas with co-immobilized BSA and with co-immobilized rat serum are identical; at concentrations of below 10 ng/ml, the calibration curve of measurement areas with co-immobilized rat serum has higher signal values than that with co-immobilized BSA. The difference in signals is assigned to the contribution of unspecific binding of the binding reagent to the ingredients of the immobilized rat serum. When even higher concentrations of rat serum are added to the immobilization solution, the signal difference with measurement areas to whose generating immobilization solutions only BSA has been added is even more pronounced.

To determine the unknown P-Akt (Ser473) concentrations in the samples prepared from rat heart tissue, use is made of the calibration curves which were generated with the aid of immobilization solutions to which only BSA has been added, since said curves enable concentrations to be determined even at low Akt concentrations, below 10 ng/ml.

b) Use of Binding Reagents with Addition of Akt as Competitor

To test the proportion of signals due to unspecific binding to the calibration curves which have been established using the immobilization solutions with different sample matrix, a mixture of the solution of the "anti-P-Akt (Ser473)" antibody as binding reagent with an excess of Akt (5 µg/ml corresponding to 100 nM) is introduced into a fifth sample container on another array with identical arrangement of the measurement areas as the array studied previously, and incubated with said measurement areas overnight, as described under 4.2. Under these conditions, the proportion of signals caused by specific binding of the antibody to immobilized P-Akt (Ser473) is expected to disappear, while the proportion of signals caused by unspecific binding remains.

As expected, complete suppression of the signal (caused by specific binding) is observed, within the accuracy of measurement, within the relevant concentration range for determining endogenous P-Akt (Ser473), namely below 100 ng/ml (empty symbols in FIG. 8). The signals from measurement areas whose immobilization solutions contained rat serum are higher than the signals of those measurement areas whose immobilization solutions contained, apart from the defined Akt concentrations, only BSA, according to the expected different proportions of unspecific binding to the sample matrix components.

The signal increase observed with the highest P-Akt (Ser473) concentrations (1000 ng/ml and 3000 ng/ml in the immobilization solution) is attributed to the fact that the competitor concentration in solution under these conditions is apparently not sufficient in order to completely prevent specific binding of the binding reagent to immobilized P-Akt (Ser473).

c) Use of Binding Reagents with Addition of Sample Matrix-Like Substances as Competitors To check the proportion of unspecific binding caused by the binding reagents binding to components of the sample matrix, rat serum with a total protein concentration of 0.1 mg/ml is added to the antibody solution. This solution is then introduced into a sixth sample container with a sixth array of again the same arrangement of measurement areas as the abovementioned arrays, according to the procedure of section 4.3. Under these conditions, the proportions of signals generated by specific binding to immobilized P-Akt (Ser473) are expected to be retained, while the proportions of signals generated by unspecific binding to the sample matrix are expected to largely disappear.

Figure 9:
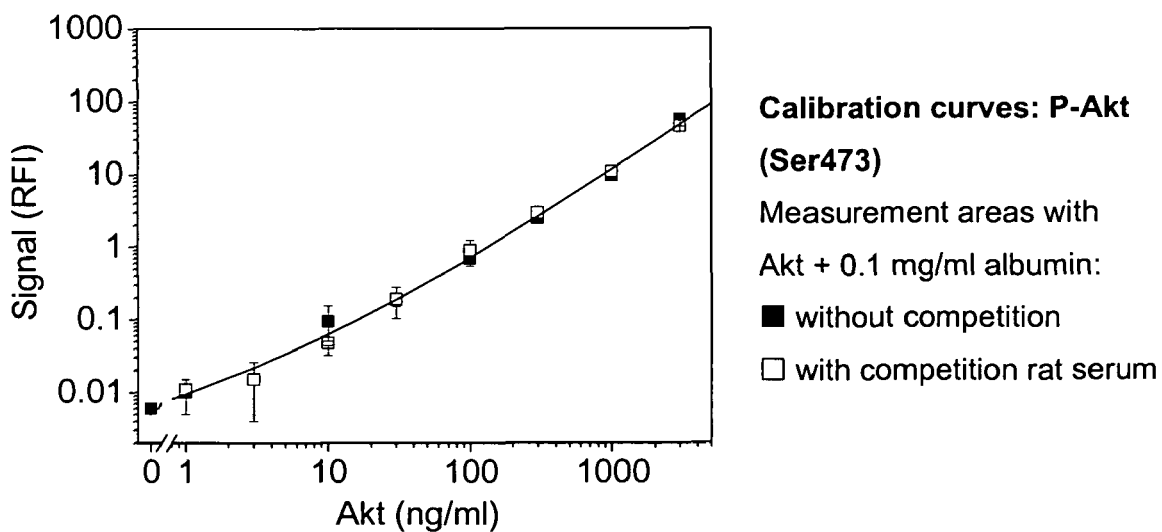
FIG. 9: referenced fluorescence intensities (RFI) from measurement areas with purified Akt applied thereto and with additional presence of 0.1 mg/ml BSA or 0.1 mg/ml rat serum in the immobilization solutions, as a function of the P-Akt (Ser473) concentration of the immobilization solutions. Filled symbols: calibration curves generated without competitor in the solution of the binding reagent ("anti-P-Akt (Ser473)" antibody, 5 nM), empty symbols: measurement curve generated with 0.1 mg/ml rat serum as competitor for unspecific binding in the solution of the binding reagent.

FIG. 9 depicts, by filled symbols, again the calibration curve described under section 7.2.1.a), generated using the fourth array without addition of competitors of the binding reagents. Deviations of the signals obtained using the sixth array by addition of the rat serum-containing solution of the antibody as binding reagent from these calibration curves cannot be measured.

This suggests that, in the case of the "anti-P-Akt (Ser473)" antibody, the generated calibration curve also corresponds with high accuracy to the specific binding events and unspecific binding to the sample matrix takes place only to a very small extent.

7.2.2. Determination of the P-Akt (Ser473) Content in Samples Prepared from Rat Heart Tissue a) Use of Binding Reagents without Addition of Competitors Detection of the P-Akt (Ser473) content in the samples of biological origin and complex composition prepared from rat heart tissue is carried out on the segment of measurement areas indicated by the measurement area contents numbers 25 to 31. The immobilization solutions generated for generating said measurement areas are from the same stock solution and were adjusted by dilution (see section 3.) to different total protein concentrations (between 0.025 mg/ml and 0.5 mg/ml).

The segment of measurement areas with the measurement area contents numbers 37 to 43 was generated by applying immobilization samples from an identical serial dilution of the stock solution from the rat heart tissue lysate, but with in each case purified Akt in a concentration of 1000 ng/ml being added to the immobilization samples. The signals to be measured with the aid of this segment are to be used for controlling, whether a high P-Akt (Ser473) content corresponding to the high "total-Akt" concentration used (which is substantially higher than the expected natural, endogenous Akt content) is recovered by comparing the fluorescence signals to be measured with the calibration curve for P-Akt (Ser473) (established using measurement areas containing co-immobilized BSA), with identical total protein concentration (0.1 mg/ml).

The measurement is carried out, in combination with the part of the process of the invention that is described under 7.2.1.a, by means of adding a solution of "anti-P-Akt (Ser473)" (5 nM) to the fourth sample container containing the fourth array of measurement areas. The further process substeps have been described previously under 4.1.

FIG. 10 depicts the results (referenced fluorescence intensities). The fluorescence signals from measurement areas to which immobilization solutions prepared from rat heart tissue were applied are depicted as a function of the total protein concentration (FIG. 10, top abscissa), and the values of the referenced fluorescence signals of the calibration measurement with co-immobilized BSA (protein concentration: 0.1 mg/ml) are depicted as a function of the P-Akt (Ser473) concentrations of the immobilization solutions utilized for these measurement areas (FIG. 10, bottom abscissa).

The signals for P-Akt (Ser473) from the measurement areas without added Akt (i.e. with endogenous P-Akt (Ser473) naturally occurring in the immobilized samples), initially increase, as expected, with increasing protein concentration and reach a maximum value, from a protein concentration of 0.2 mg/ml upward. No further signal increase is observed with further increasing protein concentration, similar to a saturation effect.

The signals from the measurement areas containing 1000 ng/ml added P-Akt (Ser473) (i.e. with endogenous P-Akt (Ser473)) naturally occurring in the immobilized samples and additionally 1000 ng/ml purified P-Akt(Ser473)) correspondingly reach very high values. This requires the purified Akt utilized for generating the calibration curves to be completely phosphorylated, i.e. phosphorylated at Ser473 and at Thr308. The P-Akt (Ser473) concentration of 1000 ng/ml added to the sample can be recovered and determined to (870±100) ng/ml by comparing the signal values with the simultaneously generated calibration curve with comparable total protein concentration (0.1 mg/ml, illustrated by the broken line at a protein concentration of 0.1 mg/ml, and by the broken line from the point of intersection of this line with the measured curve of signals from measurement areas with 1000 ng/ml added P-Akt (Ser473) in the direction of the calibration curve) (see dotted line). The achieved recovery rate of 92%. The high recovery value likewise confirms that the measured curve generated on measurement areas with 0.1 mg/ml BSA added to the immobilization solutions (as protein matrix) is well-suited to calibrate the data of spots which were prepared from solutions containing rat heart tissue lysates.

A content of (12±2) ng/ml endogenous P-Akt (Ser473) is determined for the sample prepared from rat heart tissue with a protein content of 0.1 mg/ml by comparison with the calibration curve (illustrated by the broken line at a protein concentration of 0.1 mg/ml and by the broken line from the point of intersection of this line with the measurement curve of signals from measurement areas containing only endogenous P-Akt (Ser473) in the direction of the calibration curve). This requires the purified Akt utilized for generating the calibration curves to be completely phosphorylated, i.e. phosphorylated at Ser473 and at Thr308. If the P-Akt (Ser473) portion of the purified Akt is less than 100%, the value of this measurement in the sample prepared from rat heart tissue is reduced accordingly.

b) Use of Binding Reagents with Addition of Akt as Competitor

To determine the proportion of signals due to unspecific binding to the measured curve from measurement areas which have been generated using the immobilization solutions based on rat heart tissue as sample matrix, a mixture of the solution of the "anti-P-Akt (Ser473)" antibody as binding reagent with an excess of Akt (5 µg/ml corresponding to a concentration of 100 nM) is introduced into a fifth sample container on another array with identical arrangement of the measurement areas as the array studied initially, and incubated with said measurement areas overnight, as described under 4.2. Under these conditions, the proportion of signals caused by specific binding of the antibody to immobilized P-Akt (Ser473) is expected to disappear, while the proportion of signals caused by unspecific binding remains.

FIG. 11 depicts the results of the competition experiment, together with the results of the corresponding measurements without the presence of a competitor in the solution of the binding reagent, described above under 7.2.2.a). Filled symbols indicate in each case the results without the presence of a competitor (measured on the fourth array), and empty symbols indicate the signals measured in the presence of the competitor (measured on the second array). The fluorescence signals from measurement areas whose immobilization solutions were prepared from rat heart tissue lysates (both for determining the naturally occurring endogenous P-Akt (Ser473), without additionally added Akt, measurement area contents reference numbers 25 to 31, and with 1000 ng/ml additionally added, purified Akt, measurement area contents reference numbers 37 to 43, according to FIG. 1) are depicted as a function of the protein concentration of the immobilization solution (FIG. 11, top abscissa). The calibration curve, described in 7.2.1., for detecting P-Akt (Ser473) (with 0.1 mg/ml BSA in the immobilization solutions) is plotted as a function of the P-Akt (Ser473) concentration (FIG. 11, bottom abscissa).

In the presence of the competitor, the signals from the measurement areas for determining the endogenous p473-Akt are distinctly reduced. The difference between the measured curves in the absence and in the presence of the competitor represents the proportion of signals caused by specific binding.

An even more distinct reduction of the referenced fluorescence signals is observed for the measurement areas whose immobilization solution additionally contained an excess of Akt (1000 ng/ml). The measured curves generated in the presence of 100 nM Akt as competitor in solution from the two segments of measurement areas (for determining endogenous Akt and for control measurement with 1000 ng/ml Akt in the immobilization solution) again virtually coincide. The remaining signal which increases clearly up to a protein concentration of 0.3 mg/ml and beyond that only slightly increases, corresponds to the signal contribution due to unspecific binding (to the proteins of the sample matrix), which contribution naturally increases with increasing surface concentration of the proteins, until the surface of the measurement areas is completely covered.

Figure 12:
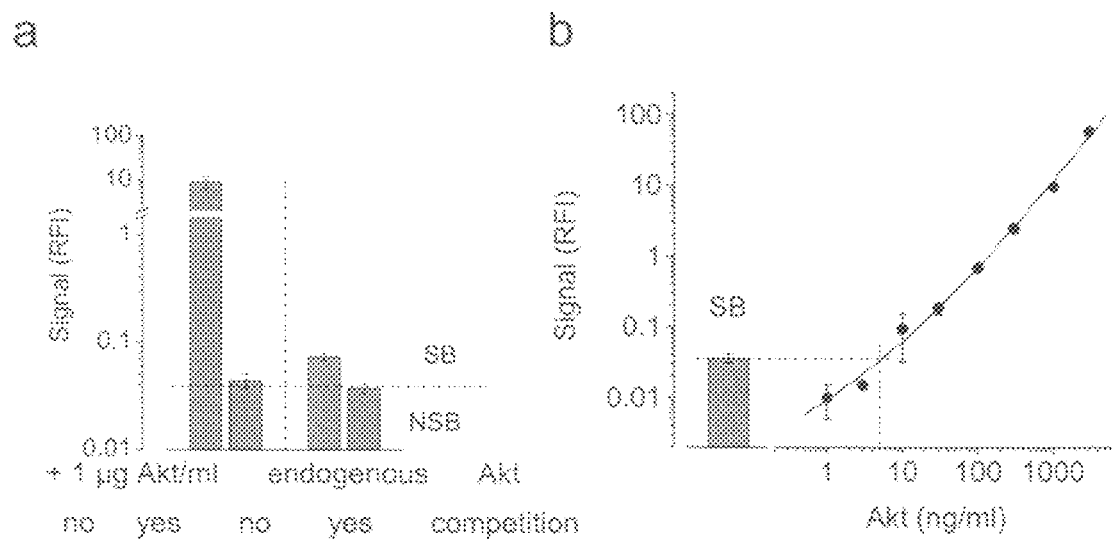
FIG. 12: determination of the proportions of the signals of FIG. 11 caused by specific binding at a protein concentration of 0.1 mg/ml from comparing the data in the presence and absence of the competitor in solution (FIG. 12*a*), and determination of the content of endogenous Akt from comparing the proportion of signal caused by specific biding ("SB") with the calibration curve (FIG. 12*b*).

FIG. 12 illustrates determination of the signal portions caused by specific binding at a protein concentration of 0.1 mg/ml from comparing the data in the absence and presence of the competitor in solution (FIG. 12a), and determination of the endogenous Akt content from comparing the signal portion caused by specific binding ("SB") with the calibration curve (FIG. 12b). The signal portions (0.037 RFI) caused by unspecific binding ("NSB") are of the same size for signals from measurement areas containing only endogenous Akt (0.073 RFI) and those containing additionally added 1000 ng/ml purified Akt (approx. 10 RFI), within the accuracy of measurement. A content of (5.3±0.5) ng/ml endogenous P-Akt (Ser473) is determined by comparing the difference between the total signal and the unspecifically caused signal with the calibration curve (FIG. 12b). Comparison with the determination of Akt in section 7.1.2.a), in which signal portions generated by unspecific binding were not discriminated, indicates that about 57% of the P-Akt (Ser473) content provisionally determined there must be assigned to the contribution of unspecific binding.

c) Use of Binding Reagents with Addition of Substances Similar to the Sample Matrix as Competitors To check the proportion of unspecific binding caused by the binding reagents binding to components of the sample matrix, rat serum with a total protein concentration of 0.1 mg/ml is added to the antibody solution. This solution is then introduced into a sixth sample container with a sixth array of again the same arrangement of measurement areas as the abovementioned first and second arrays, according to the procedure of section 4.3. Under these conditions, the proportions of signals generated by specific binding to immobilized P-Akt (Ser473) are expected to be retained, while the proportions of signals generated by unspecific binding to the sample matrix are expected to largely disappear.

Figure 13:
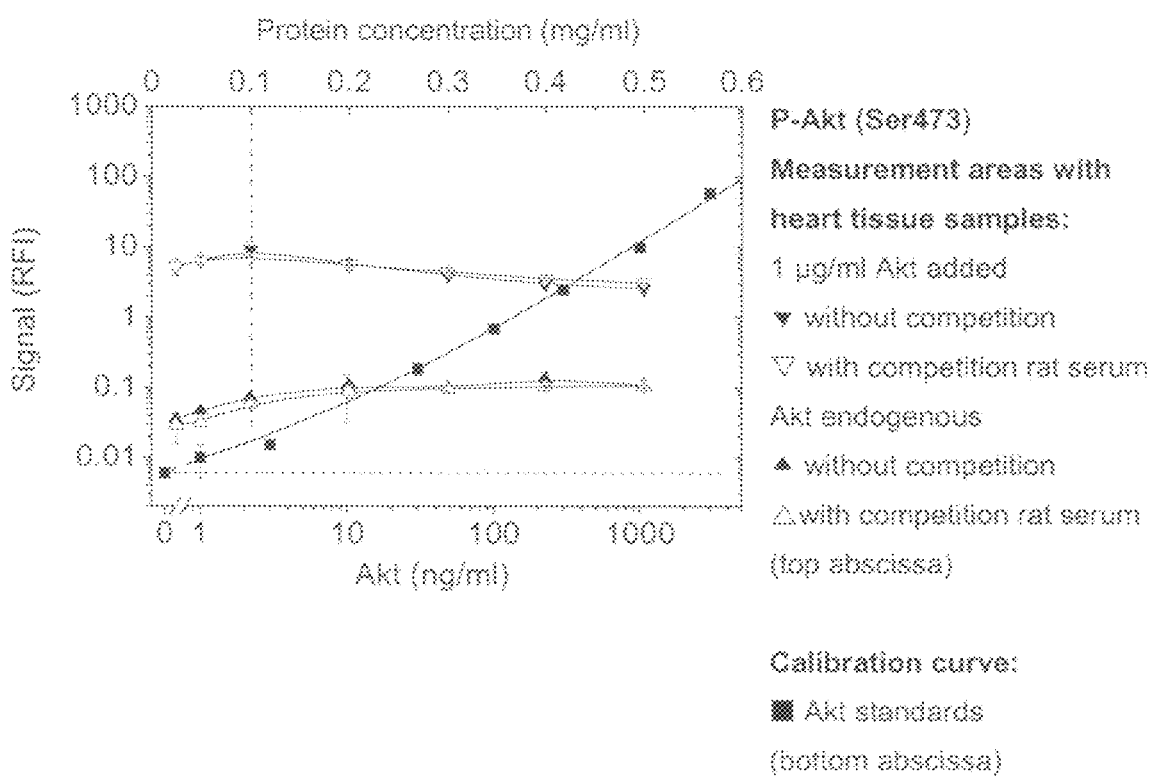
FIG. 13: referenced fluorescence intensities for detecting endogenous P-Akt (Ser473) in samples prepared from rat heart tissue, with (top curve) and without (middle curve) additionally added purified Akt (1000 ng/ml), as a function of total protein concentration of the immobilization solutions (top abscissa). Filled symbols: data obtained from measurement without competitor in the solution of the binding reagent ("anti-P-Akt (Ser473)" antibody, 5 nM); empty symbols: data obtained from measurement with 0.1 mg/ml rat serum as competitor for unspecific binding in the solution of the binding reagent ("anti-P-Akt (Ser473)" antibody, 5 nM). Also plotted are the calibration curve of FIG. 8 for detecting P-Akt (Ser473), generated with measurement areas additionally containing 0.1 mg/nm BSA (filled symbols; as function of the P-Akt (Ser473) concentration, bottom abscissa) and a corresponding calibration curve, generated with 0.1 mg/ml rat serum as competitor for unspecific binding in the solution of the binding reagent (empty symbols; as function of the P-Akt (Ser473) concentration, bottom abscissa).

The results of the competition experiment with rat serum in solution are depicted in FIG. 13, together with the results of the corresponding measurements, described above under 7.2.2.a), without the presence of a competitor in the solution of the binding reagent. Filled symbols indicate in each case the results without the presence of a competitor (measured on the fourth array), and empty symbols indicate the signals measured in the presence of the competitor (measured on the sixth array). The fluorescence signals from measurement areas whose immobilization solutions were prepared from rat heart tissue lysates (both for determining the naturally occurring endogenous P-Akt (Ser473), without additionally added Akt, measurement area contents reference numbers 25 to 31, and with 1000 ng/ml additionally added Akt, measurement area contents reference numbers 37 to 43, according to FIG. 1) are depicted as a function of the protein concentration of the immobilization solution (FIG. 13, top abscissa). The calibration curve, described in 7.2.1.a), for detecting P-Akt (Ser473) (with 0.1 mg/ml BSA in the immobilization solutions) is plotted as a function of the P-Akt (Ser473) concentration (FIG. 13, bottom abscissa).

The presence of rat serum in solution as competitor for unspecific binding in solution does not result in any significant shift of the measured curves; the referenced fluorescence signals measured in the presence and absence of rat serum are in each case identical, within the accuracy of measurement.

This suggests that, in the case of the "anti-P-Akt (Ser473)" antibody there is no significant unspecific binding to the sample matrix.

7.3. Determination of the P-Akt (Thr308) Content 7.3.1. Calibration Curves for Detecting P-Akt (Thr308)

a) Use of Binding Reagents without Addition of Competitors

Calibration curves for determining the phosphorylated form, P-Akt (Thr308), are established by using segments of identical measurement areas, in the manner of the above-described determination of Akt and of P-Akt (Ser473).

Segment 1: array rows I and II with measurement area contents numbers 1-9 with applied different concentrations (between 0 ng/ml and 3000 ng/ml) of purified Akt in spotting buffer additionally containing 0.1 mg/ml BSA, segment 2: array rows III and IV with measurement area contents numbers 13-21 with applied different concentrations (between 0 ng/ml and 3000 ng/ml) of purified Akt in spotting buffer additionally containing 0.1 mg/ml rat serum. The purified Akt is assumed to be completely phosphorylated, i.e. phosphorylated at Ser473 and at Thr308.

Figure 14:
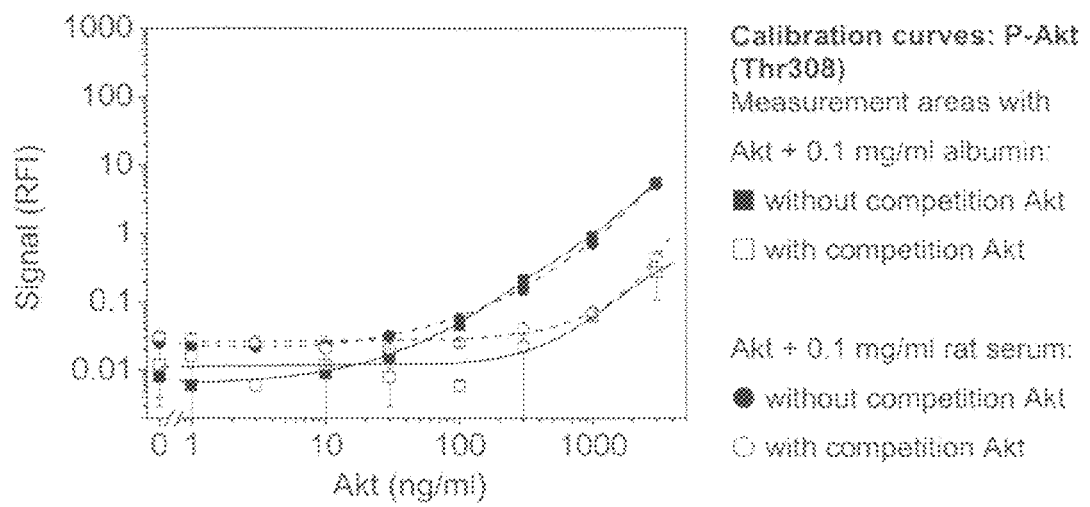
FIG. 14: referenced fluorescence intensities (RFI) from measurement areas with purified Akt applied thereto and with additional presence of 0.1 mg/ml BSA or 0.1 mg/ml rat serum in the immobilization solutions, as a function of the assumed P-Akt (Thr308) concentration of the immobilization solutions. Filled symbols: calibration curves generated without competitor in the solution of the binding reagent ("anti-P-Akt (Thr308)" antibody, 5 nM), empty symbols: measurement curves generated with 100 nM Akt as competitor in the solution of the binding reagent.

A solution of anti-P-Akt (Thr308) (5 nM) is added to a seventh sample container containing a seventh array of measurement areas. The other process substeps have been described previously under 4.1. The calibration curves of segment 1 of measurement areas (generated using solutions containing different concentrations of Akt and 0.1 mg/ml BSA added to the spotting buffer) and of segment 2 of measurement areas (generated using solutions containing different Akt concentrations and 0.1 mg/ml rat serum added to the spotting buffer) are depicted in FIG. 14 (filled symbols).

At concentrations of above 100 ng/ml Akt, the calibration curves of measurement areas with co-immobilized BSA and with co-immobilized rat serum are identical; at concentrations of below 100 ng/ml, the calibration curve of measurement areas with co-immobilized rat serum has higher signal values than that with co-immobilized BSA; the difference in signals is assigned to the contribution of unspecific binding of the binding reagent to the ingredients of the immobilized rat serum. The measured signal values from both kinds of measurement areas are relatively low, however, in comparison to the fluorescence signals which had been measured when establishing the calibration curves for Akt and P-Akt (Ser473).

To determine the unknown P-Akt (Thr308) concentrations in the samples prepared from rat heart tissue, use is made of the calibration curves which were generated with the aid of immobilization solutions to which only BSA has been added.

b) Use of Binding Reagents with Addition of Akt as Competitor

To test the proportion of signals due to unspecific binding to the calibration curves which have been established using the immobilization solutions with different sample matrix, a mixture of the solution of the "anti-P-Akt (Thr308)" antibody as binding reagent with an excess of Akt (5 µg/ml corresponding to 100 nM) is introduced into an eighth sample container on another array with identical arrangement of the measurement areas as the array studied previously, and incubated with said measurement areas overnight, as described under 4.2. Under these conditions, the proportion of signals caused by specific binding of the antibody to immobilized P-Akt (Thr308) is expected to disappear, while the proportion of signals caused by unspecific binding remains.

Only at high concentrations of the immobilization solutions, above 30 ng/ml, a decrease in the signals is determined (empty symbols in FIG. 14, with the signals from measurement areas whose immobilization solutions contained rat serum being higher than the signals of those measurement areas whose immobilization solutions contained, apart from the defined Akt concentrations, only BSA. Only in the concentration range of more than about 30 ng/ml, signal decrease exceeds experimentally caused signal variation, due to the presence of P-Akt (Thr308) as competitor in the solution of the binding reagent.

This leads to the conclusion that unspecific binding of the anti-P-Akt (Thr308) antibody both to measurement areas with co-immobilized BSA and with co-immobilized serum components takes place to a considerable extent.

c) Use of Binding Reagents with Addition of Sample Matrix-Like Substances as Competitors To check the proportion of unspecific binding to fluorescence signals caused by binding of the binding reagents to components of the sample matrix, rat serum with a total protein concentration of 0.1 mg/ml is added to the solution of the antibody. This solution is then introduced into a ninth sample container with a ninth array of again the same arrangement of measurement areas as the abovementioned arrays, according to the procedure of section 4.3. Under these conditions, the proportions of signals generated by specific binding to immobilized P-Akt (Thr308) are expected to be retained, while the proportions of signals generated by unspecific binding to the sample matrix are expected to largely disappear.

Figure 15:
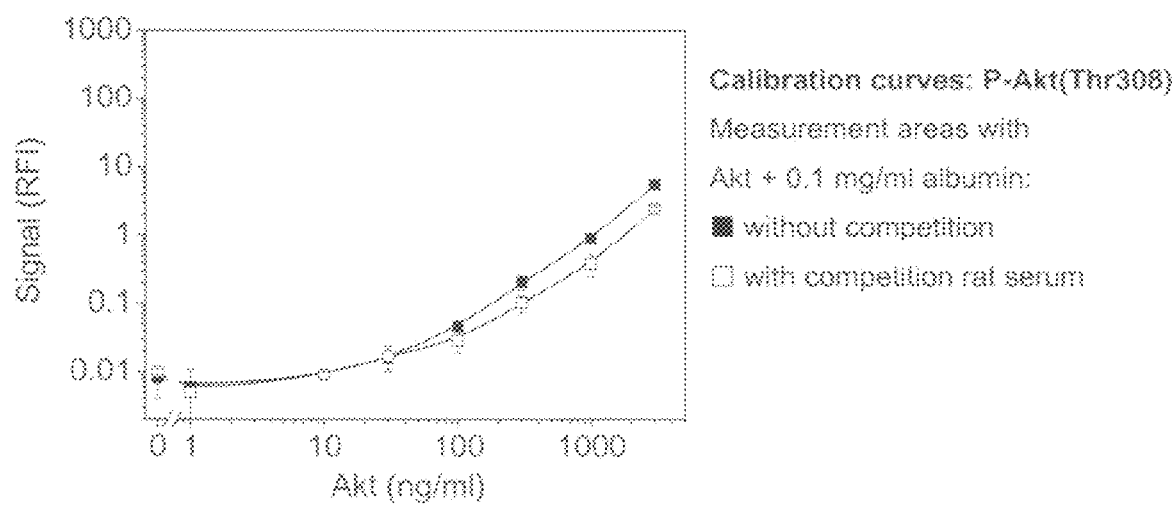
FIG. 15: referenced fluorescence intensities (RFI) from measurement areas with purified Akt applied thereto and with additional presence of 0.1 mg/ml BSA or 0.1 mg/ml rat serum in the immobilization solutions, as a function of the assumed P-Akt (Thr308) concentration of the immobilization solutions. Filled symbols: calibration curves generated without competitor in the solution of the binding reagent ("anti-P-Akt (Thr308)" antibody, 5 nM), empty symbols: measurement curve generated with 0.1 mg/ml rat serum as competitor for unspecific binding in the solution of the binding reagent.

FIG. 15 depicts, by filled symbols, again the calibration curve described under section 7.3.1.a), generated using the seventh array without addition of competitors of the binding reagents. Deviations of the signals obtained using the ninth array by addition of the rat serum-containing solution of the antibody as binding reagent from these calibration curves cannot be measured. A significant dependence on the assumed concentration of P-Akt (Thr308) in the immobilization solution is found only at concentrations above 30 ng/ml. This is consistent with the fact that fluorescence signals measured at lower concentrations can be attributed to unspecific binding.

7.3.2. Determination of the P-Akt (Thr308) Content in Samples Prepared from Rat Heart Tissue a) Use of Binding Reagents without Addition of Competitors Detection of the P-Akt (Thr308) content in the samples of biological origin and complex composition prepared from rat heart tissue is carried out on the segment of measurement areas indicated by the measurement area contents numbers 25 to 31. The immobilization solutions generated for generating said measurement areas are from the same stock solution and were adjusted by dilution (see section 3.) to different total protein concentrations (between 0.025 mg/ml and 0.5 mg/ml).

The segment of measurement areas with the measurement area contents numbers 37 to 43 was generated by applying immobilization samples from an identical serial dilution of the stock solution from the rat heart tissue lysate, but with in each case purified Akt in a concentration of 1000 ng/ml being added to the immobilization samples. The signals to be measured with the aid of this segment are to be used for controlling, whether a high P-Akt (Thr308) content corresponding to the high "total-Akt" concentration used (which is substantially higher than the expected natural, endogenous Akt content) is recovered by comparing the fluorescence signals to be measured with the calibration curve for P-Akt (Thr308) (established using measurement areas containing co-immobilized BSA), with identical total protein concentration (0.1 mg/ml).

The measurement is carried out, in combination with the part of the process of the invention that is described under 7.3.1.a, by means of adding a solution of "anti-P-Akt (Thr308)" (5 nM) to the seventh sample container containing the seventh array of measurement areas. The further process substeps have been described previously under 4.1.

FIG. 16 depicts the results (referenced fluorescence intensities). The fluorescence signals from measurement areas to which immobilization solutions prepared from rat heart tissue were applied are depicted as a function of the total protein concentration (FIG. 16, top abscissa), and the values of the referenced fluorescence signals of the calibration measurement with co-immobilized BSA (protein concentration: 0.1 mg/ml) are depicted as a function of the assumed P-Akt (Thr308) concentrations of the immobilization solutions utilized for these measurement areas (FIG. 16, bottom abscissa).

The signals for P-Akt (Thr308) from the measurement areas without added Akt (i.e. with endogenous P-Akt (Thr308) occurring naturally in the immobilized samples) increase to 0.4 mg/ml with increasing protein concentration and reach a maximum value there which does not change substantially at a protein concentration of 0.5 mg/ml.

A content of (130±15) ng/ml endogenous P-Akt (Thr308) is determined (provisionally) for the sample prepared from rat heart tissue with a protein content of 0.1 mg/ml by comparison with the calibration curve (illustrated by the broken line at a protein concentration of 0.1 mg/ml and by the broken line from the point of intersection of this line with the measurement curve of signals from measurement areas containing only endogenous P-Akt (Thr308) in the direction of the calibration curve). However, this value must be regarded as unrealistic from the start, in view of a "total-Akt" concentration of 20 ng/ml determined previously under the same conditions (without taking into account effects of unspecific binding), with the same total protein concentration. Comparison (illustrated by the broken line at a protein concentration of 0.1 mg/ml, and by the broken line from the point of intersection of this line with the measured curve of signals from measurement areas with 1000 ng/ml added Akt in the direction of the calibration curve) of the measured curve with signals from measurement areas to whose immobilization solutions 1000 ng/ml purified Akt have been added, determines a recovery value of (510±10) ng/ml.

b) Use of Binding Reagents with Addition of Akt as Competitor

To determine the proportion of signals due to unspecific binding to the measured curve from measurement area which have been generated using the immobilization solutions based on rat heart tissue as sample matrix, a mixture of the solution of the "anti-P-Akt (Thr308)" antibody as binding reagent with an excess of Akt (5 µg/ml corresponding to a concentration of 100 nM) is introduced into an eighth sample container on another array with identical arrangement of the measurement areas as the array studied initially, and incubated with said measurement areas overnight, as described under 4.3. Under these conditions, the proportion of signals caused by specific binding of the antibody to immobilized P-Akt (Thr308) is expected to disappear, while the proportion of signals caused by unspecific binding remains.

FIG. 17 depicts the results of the competition experiment, together with the results of the corresponding measurements without the presence of a competitor in the solution of the binding reagent, described above under 7.3.2.a). Filled symbols indicate in each case the results without the presence of a competitor (measured on the first array), and empty symbols indicate the signals measured in the presence of the competitor. The fluorescence signals for measurement areas whose immobilization solutions were prepared from rat heart tissue lysates (both for determining the naturally occurring endogenous P-Akt (Thr308), without additionally added Akt, measurement area contents reference numbers 25 to 31, and with 1000 ng/ml additionally added, purified Akt, measurement area contents reference numbers 37 to 43, according to FIG. 1) are depicted as a function of the protein concentration of the immobilization solution (FIG. 15, top abscissa). The calibration curve, described in 7.3.1., for detecting P-Akt (Thr308) (with 0.1 mg/ml BSA in the immobilization solutions) is plotted as a function of the assumed P-Akt (Thr308) concentration (FIG. 17, bottom abscissa).

In the presence of the competitor, the signals from the measurement areas for determining the endogenous P-Akt (Thr308) show no reduction whatsoever. The difference between the measured curves in the absence and presence of the competitor, which would represent the signal portion caused by specific binding, is zero, within the accuracy of measurement.

A comparatively weak reduction in the referenced fluorescence signals is observed, especially in the low protein concentration range, for the measurement areas whose immobilization solution additionally contained an excess of Akt (1000 ng/ml).

Figure 18:
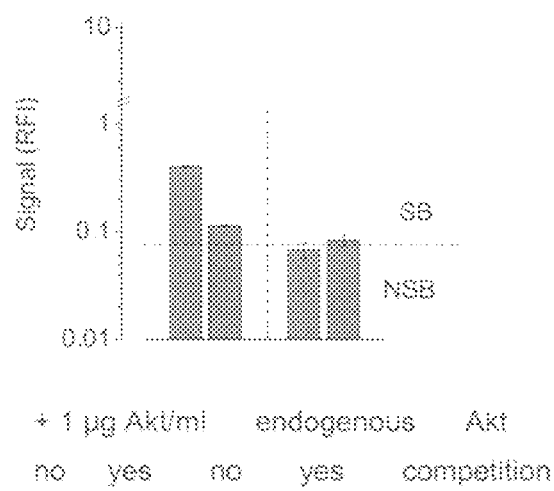
FIG. 18: determination of the proportions of the signals of FIG. 17 caused by specific binding at a protein concentration of 0.1 mg/ml from comparing the data in the presence and absence of the competitor in solution.

FIG. 18 illustrates determination of the signal portions caused by specific binding at a protein concentration of 0.1 mg/ml by comparing the data in the presence and absence of the competitor in solution. Signals of 0.068 RFI from the measurement without competitor and of 0.073 RFI from the measurement with 100 nM competitor are determined for the measurement areas generated from solutions of rat heart tissue lysates, where at most the presence of endogenous P-Akt (Thr308) is expected. The difference between these two values corresponds approximately to the experimentally caused signal variation. This confirms that no signal generated by specific binding is measured under the present conditions, leading to the possible conclusion that the P-Akt (Thr308) content is zero.

c) Use of Binding Reagents with Addition of Substances Similar to the Sample Matrix as Competitors To check the proportion of unspecific binding caused by the binding reagents binding to components of the sample matrix, rat serum with a total protein concentration of 0.1 mg/ml is added to the antibody solution. This solution is then introduced into a ninth sample container with a ninth array of again the same arrangement of measurement areas as the abovementioned arrays, according to the procedure of section 4.3. Under these conditions, the proportions of signals generated by specific binding to immobilized P-Akt (Thr308) are expected to be retained, while the proportions of signals generated by unspecific binding to the sample matrix are expected to largely disappear.

Figure 19:
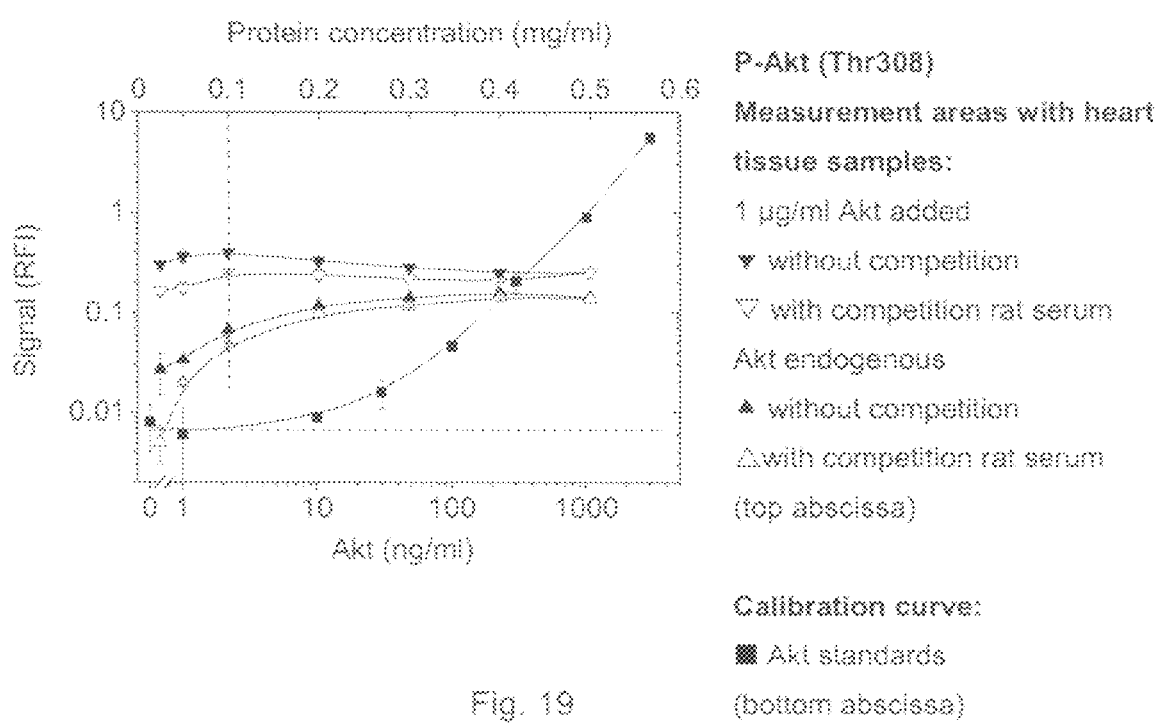
FIG. 19: referenced fluorescence intensities for detecting endogenous P-Akt (Thr308) in samples prepared from rat heart tissue, with (top curve) and without (middle curve) additionally added purified Akt (1000 ng/ml), as a function of total protein concentration of the immobilization solutions (top abscissa). Filled symbols: data obtained from measurement without competitor in the solution of the binding reagent ("anti-P-Akt (Thr308)" antibody, 5 nM); empty symbols: data obtained from measurement with 0.1 mg/ml rat serum as competitor for unspecific binding in the solution of the binding reagent ("anti-P-Akt (Thr308)" antibody, 5 nM). Also plotted are the calibration curve of FIG. 12 for detecting P-Akt (Thr308), generated with measurement areas additionally containing 0.1 mg/ml BSA (filled symbols; as function of the assumed P-Akt (Thr308) concentration, bottom abscissa) and a corresponding calibration curve, generated with 0.1 mg/ml rat serum as competitor for unspecific binding in the solution of the binding reagent (empty symbols; as function of the assumed P-Akt (Thr308) concentration, bottom abscissa).

The results of the competition experiment with rat serum in solution are depicted in FIG. 19, together with the results of the corresponding measurements, described above under 7.3.2.a), without the presence of a competitor in the solution of the binding reagent. Filled symbols indicate in each case the results without the presence of a competitor (measured on the seventh array), and empty symbols indicate the signals measured in the presence of the competitor. The fluorescence signals from measurement areas whose immobilization solutions were prepared from rat heart tissue lysates (both for determining the naturally occurring endogenous P-Akt (Thr308), without additionally added Akt, measurement area contents reference numbers 25 to 31, and with 1000 ng/ml additionally added Akt, according to FIG. 1) are depicted as a function of the protein concentration of the immobilization solution (FIG. 19, top abscissa). The calibration curve, described in 7.3.1.a), for detecting P-Akt (Thr308) (with 0.1 mg/ml BSA in the immobilization solutions) is plotted as a function of the assumed P-Akt (Thr308) concentration (FIG. 19, bottom abscissa).

The presence of rat serum in solution as competitor for unspecific binding in solution results in measurable decreases in fluorescence signals, confirming once more the source of unspecific binding.

The invention claimed is:

1. A process for detecting one or more analytes in one or more samples of biological origin and complex composition, comprising the following steps:
    (1) providing one or more samples of biological origin and complex composition,
    (2) providing at least one solid support,
    (3) applying small amounts of said samples of biological origin and complex composition, in diluted or undiluted form, to discrete sites either directly on said solid support or, after previous application of an adhesion-promoting layer, to said adhesion-promoting layer on the solid support, thereby generating one or more arrays of discrete measurement areas on the at least one solid support,
    (4) contacting at least one array of discrete measurement areas with a first solution comprising one or more binding reagents as specific binding partners for the analytes to be detected and present in discrete measurement areas in the applied samples of biological origin and complex composition, and, optionally if required, one or more detection reagents, it being possible for binding reagents and detection reagents to be applied simultaneously or sequentially, (5) measuring in a space-resolved manner first optical signals emitting from discrete measurement areas of one or more arrays which have been contacted with the first solution in step (4), (6) recording said first optical signals, wherein the proportion of the first optical signals measured that are optical signals generated due to unspecific interaction with the binding reagents added and with the detection reagents optionally added is determined by carrying out the following further steps:

(7a) applying a second solution comprising, in addition to the one or more binding reagents and optionally one or more detection reagents of the first solution added in step (4), a known high concentration of compounds which are of the same kind as the analytes to be detected and present in samples of biological origin and complex composition, which samples have been applied to discrete measurement areas, as competitors to said analytes to be detected and present in samples of biological origin and complex composition, which samples have been applied to discrete measurement areas, for specific binding of said binding reagents and of optionally additionally added detection reagents, to one or more arrays of discrete measurement areas generated in step (3), and/or (7b) applying a third solution comprising, in addition to said one or more binding reagents and optionally one or more detection reagents of the first solution added in step (4), a known high concentration of substances which are of a similar kind as substances present in the sample matrix of the samples applied in step (3), for the purpose of competing with the substances of the sample matrix, which are present in the samples of biological origin and complex composition which have been applied to discrete measurement areas, for unspecific binding of said binding reagents and of optionally additionally added detection reagents, to one or more arrays of discrete measurement areas generated in step (3), (8) measuring in a space-resolved manner second and/or third optical signals emitting from discrete measurement areas of one or more arrays which have been contacted with the second solution in step (7a) and/or with the third solution in step (7b), (9) recording said second and/or third optical signals, and

(10) comparing said first and second and/or third optical signals and calculating the concentration or amount of an analyte in a sample of biological origin and complex composition which sample has been applied to a measurement area to be determined from the difference between the first optical signal of step (5) measured for said measurement area and the proportion of optical signal generated due to unspecific interaction with the added binding reagents recorded in step (9) and optionally with the added detection reagents and by comparing said difference with a calibration curve for the analyte in question.

2. The process as claimed in claim 1, wherein said samples of biological origin and complex composition are selected from the group of samples which is formed by lysates of cell populations, cell extracts, body fluids and components of body fluids, with:

(1) said samples being fractionated or non-fractionated samples, (2) said samples of biological origin and complex composition having been obtained from healthy and/or diseased and/or stimulated and/or untreated cells from the group comprising human, animal, bacterial and plant cells, (3) said samples of biological origin and complex composition having been obtained from animal or human tissue such as, for example, organ, skin, hair, muscle, fat or bone tissue.

3. The process as claimed in either of claims 1 and 2, wherein the material of a sample to be analyzed of biological origin and complex composition, which has been applied to a single measurement area, corresponds to the material of less than 100 cells, preferably of less than 10 cells, and/or constitutes a volume of less than 100 nl, preferably less than 1 nl.

4. The process as claimed in claim 1, wherein the analytes which are to be detected in the samples of biological origin and complex composition, which have been applied to discrete measurement areas, are proteins and posttranslationally modified protein forms thereof, and also artificially modified or expressed proteins, mono-or polyclonal antibodies and antibody fragments, peptides, peptide fragments generated from intact proteins, glycopeptides, lectins, fluorescent proteins, avidin, streptavidin, biotin, biotinylated proteins and/or differently conjugated proteins, oligosaccharides and nucleic acids.

5. The process as claimed in claim 4, wherein proteins which are to be detected as analytes in the samples of biological origin and complex composition, which have been applied to discrete measurement areas, are distinguished according to their presence in phosphorylated and/or glycosylated, and/or methylated and/or acetylated form in said applied samples of biological origin and complex composition, in the course of step (4) as claimed in claim 1 after binding of binding reagents contacted therewith as specific binding partners, and optionally of additional detection reactions, and detected separately in the detection step (5) as claimed in claim 1.

6. The process as claimed in claim 4, wherein proteins which are to be detected as analytes in the samples of biological origin and complex composition, which have been applied to discrete measurement areas, are not distinguished according to their presence in phosphorylated and/or glycosylated, and/or methylated and/or acetylated form in said applied samples of biological origin and complex composition, in the course of step (4) as claimed in claim 1 after binding of binding reagents contacted therewith as specific binding partners, and optionally of additional detection reactions, and not detected separately in the detection step (5) as claimed in claim 1.

7. The process as claimed in claim 1, wherein said binding reagents, as specific binding partners of the analytes to be detected and present in discrete measurement areas in the applied samples of biological origin and complex composition, are selected from the group of compounds which comprises proteins, peptides, enzymes, enzyme inhibitors, kinase substrates, aptamers, synthetic peptide structures, glycopeptides, hormones, cofactors, oligosaccharides, lectins, antigens for antibodies or T-cell receptors, biotin, avidin, streptavidin, proteins functionalized with additional binding sites and/or complex formation partners thereof as well as nucleic acid analogs and their derivatives having artificial bases.

8. The process as claimed in claim 1, wherein said detection reagents are selected from:

(1) a first group which comprises polyclonal or monoclonal antibodies and antibody fragments, nucleic acids and nucleic acid derivatives and their derivatives having artificial bases, biotin, avidin, streptavidin and neutravidin, or (2) a second group which comprises mass labels and/or luminescent labels, said mass or luminescent labels being bound to the binding reagents or attaching or binding thereto or being bound to detection reagents of the first group of detection reagents according to (1) or binding or attaching in a specific way to said detection reagents of the first group of detection reagents according to (1) or binding or attaching to the complexes between the analytes to be detected which are present in the samples of biological origin and complex composition which have been applied to discrete measurement areas, and binding reagents bound thereto as specific binding partners, are formed.

9. The process as claimed in claim 1, wherein said binding reagents as specific binding partners and optional detection reagents of a first solution and/or
binding reagents as specific binding partners, compounds of the same kind as the analytes to be detected and present in samples of biological origin and complex composition, which samples have been applied to discrete measurement areas, and optional detection reagents of a second solution and/or
binding reagents as specific binding partners, substances which are of a similar kind as substances present in the sample matrix of the samples applied in step (3) as claimed in claim 1, and comprise optional detection reagents of a third solution, are preincubated with one another in each case, and said first, second or third solution is then contacted in a single addition step with said arrays of measurement areas.

10. The process as claimed in claim 1, wherein different analytes are detected in a shared array of measurement areas by adding distinguishable detection reagents to said array.

11. The process as claimed in claim 10, wherein the number of different analytes to be detected is equal to the number of distinguishable detection reagents.

12. The process as claimed in claim 10, wherein distinguishable detection reagents differ in the excitation wavelength and/or emission wavelength of a luminescence.

13. The process as claimed in claim 1, wherein a multiplicity of different analytes in a multiplicity of arrays of discrete measurement areas are detected by adding different binding reagents as specific binding partners for determining different analytes on various arrays of discrete measurement areas and/or by adding distinguishable detection reagents to said arrays of measurement areas.

14. The process as claimed in claim 1, wherein different binding reagents are applied as specific binding partners for different analytes to various arrays for each different analyte to be detected.

15. The process as claimed in claim 1, wherein arrays of measurement areas containing samples of biological origin and complex composition applied thereto comprise those measurement areas in which known concentrations of compounds which are of the same kind as the analytes to be detected have been added as standards to the applied material.

16. The process as claimed in claim 15, wherein arrays of measurement areas comprise a number of those measurement areas in which different known concentrations of compounds which are of the same kind as the analytes to be detected have been added as standards to the applied material, the number of such measurement areas and the level of said different known concentrations being sufficient in order to generate, by means of a single step of adding a first solution containing binding reagents as specific binding partners and optionally likewise detection reagents according to step (4) as claimed in claim 1, and of subsequent steps (5) and (6) as claimed in claim 1, a calibration curve for determining unknown concentrations of said analytes to be detected in the array.

17. The process as claimed in claim 1, wherein a plurality of the same kind of arrays of measurement areas are arranged on a solid support, with identical positions of measurement areas in various arrays, with regard to arrangement in rows and columns, meaning that samples of the same kind have been applied there.

18. The process as claimed in claim 1, wherein a first solution according to step (4) is added and first optical signals from the measurement areas of this array are measured and recorded according to steps (5) and (6) as claimed in claim 1, and second and/or third solutions according to steps (7a) and (7b) are added and the signals emitted from the measurement areas of the arrays in question are subsequently measured and recorded according to steps (8) and (9) as claimed in claim 1, on various measurement area arrays of the same kind, with identical positions of measurement areas in various arrays, with regard to arrangement in rows and columns, meaning that samples of the same kind have been applied there.

19. The process as claimed in claim 1, wherein the proportion of the measured first optical signals according to claim 1 that are optical signals generated due to unspecific interaction with the added binding reagents and optionally with the added detection reagents is determined from the difference of the optical signals measured according to step (8), after addition of the second solution according to step (7a), and the optical signals measured according to step (5), after addition of the first solution according to step (4).

20. The process as claimed in claim 1, wherein the proportion of the measured first optical signals according to claim 1 that are optical signals generated due to unspecific interaction with the added binding reagents and optionally with the added detection reagents is determined from the difference of the optical signals measured according to step (8), after addition of the third solution according to step (7b), and the optical signals measured according to step (5), after addition of the first solution according to step (4).

21. The process as claimed in claim 1, wherein the concentration or amount of an analyte in a sample of biological origin and complex composition, which sample has been applied to a measurement area, is determined from the difference between the optical signal measured for said measurement area and the proportion of optical signal generated due to unspecific interaction with the added binding reagents and optionally with the added detection reagents and by comparing said difference with a calibration curve for the analyte in question.

22. The process as claimed in claim 1, wherein differences, preferably of less than 20%, particularly preferably of less than 10%, in the concentration or amount of an analyte in various samples of biological origin and complex composition, which have been applied to various measurement areas, are determined.

23. The process as claimed in claim 1, wherein a third solution applied according to step (7b) as claimed in claim 1 to one or more arrays of measurement areas comprises substances from the group comprising albumins, in particular bovine serum albumin (BSA), immunoglobulins and diluted serum.

24. The process as claimed in claim 1, wherein an adhesion-promoting layer applied to the solid support comprises compounds of the group comprising silanes, functionalized silanes, epoxides, functionalized, charged or polar polymers and "self-assembled passive or functionalized mono- and multilayers", thiols, alkyl phosphates and alkyl phosphonates, and multifunctional block copolymers.

25. The process as claimed in claim 1, wherein areas between the discrete measurement areas "are passivated" for minimizing unspecific binding of binding or detection reagents by application of components which are "chemically neutral" toward said binding reagents and/or detection reagents between the spatially separated measurement areas.

26. The process as claimed in claim 1, wherein the solid support is essentially planar and/or non-porous and/or essentially optically transparent at at least the wavelength of an incident excitation light or measurement light.

27. The process as claimed in claim 1, wherein the solid support comprises a plurality of layers with different optical properties.

28. The process as claimed in claim 1, wherein the solid support comprises a metal layer, preferably comprising gold, silver or aluminum.

29. The process as claimed in claim 1, wherein at least the layer of the solid support, which is in contact with the measurement areas directly or via an adhesion-promoting layer, is essentially optically transparent at least at the wavelength of an incident excitation light or measurement light.

30. The process as claimed in claim 1, wherein the solid support comprises components from the group comprising microscope slides, microtiter plates, nanotiter plates, filters, membranes and microstructured supports.

31. The process as claimed in claim 1, wherein the solid support comprises an optical waveguide which is either continuous or divided into discrete wave-guiding regions and which comprises one or more layers.

32. The process as claimed in claim 1, wherein the excitation light or measurement light is guided from one or more polychromatic or monochromatic light sources to one or more measurement areas of one or more arrays of measurement areas and optical signals from said measurement areas and/or changes or differences in the optical signals emitting from said measurement areas are measured and recorded in a space-resolved manner.

33. The process as claimed in claim 32, wherein the changes or differences in optical signals, to be measured in a space-resolved manner, are based on local differences in the effective refractive index at the surface of the solid support, which faces the measurement areas, or within a distance of less than 1 µm from said surface of said solid support, which local differences are caused by binding reagents and/or detection reagents binding to analytes present in discrete measurement areas in the samples of biological origin and complex composition which have been applied there.

34. The process as claimed in claim 33, wherein the changes or differences in optical signals, to be measured in a space-resolved manner, are based on local differences in the resonance conditions for generating a surface plasmon in a thin metal layer as part of said solid support.

35. The process as claimed in claim 31, wherein the solid support comprises an optical thin-film waveguide having a first, essentially optically transparent layer (a) upon a second, essentially optically transparent layer (b), with layer (a) having a higher refractive index than layer (b) and being in contact with the measurement areas either directly or by mediation via an adhesion-promoting layer.

36. The process as claimed in claim 31, wherein the excitation light or measurement light from one or more light sources is coupled into a wave-guiding layer of the solid support through one or more optical coupling elements which are selected from the group of prism couplers, evanescent couplers with optical waveguides brought into contact with each other and having overlapping evanescent fields, end face couplers with focusing lenses, preferably cylindrical lenses, arranged in front of an end side of the wave-guiding layer, and grating couplers, said excitation light or measurement light preferably being coupled into a wave-guiding layer of the solid support with the aid of one or more grating structures (c) which are developed in said wave-guiding layer as surface relief gratings having a certain grating period and grating depth.

37. The process as claimed in claim 31, wherein the changes or differences in optical signals, to be measured in a space-resolved manner, are based on local differences in the resonance conditions for coupling excitation light or measurement light of one or more light sources into a wave-guiding layer of the solid support by means of a grating structure developed in said wave-guiding layer.

38. The process as claimed in claim 1, wherein the changes or differences in optical signals, to be measured in a space-resolved manner, are based on local differences or changes in one or more luminescence events which are caused by binding reagents and/or detection reagents binding to analytes present in discrete measurement areas in the samples of biological origin and complex composition which have been applied there.

39. The process as claimed in claim 32, wherein
the solid support comprises an optical thin-film waveguide with a first layer (a) which is essentially optically transparent at at least the wavelength of an incident excitation light upon a second layer (b) which is essentially optically transparent at least at the wavelength of an incident excitation light and which has a lower refractive index than layer (a),
excitation light of a light source is coupled into the layer (a) by means of a grating structure (c) developed in said layer (a),
said excitation light is guided as a guided wave to measurement areas which are located either directly on said layer (a) or by mediation via an adhesion-promoting layer on said layer (a), and
luminescence events of compounds which are capable of luminescence and which are excited in the evanescent field of the light guided in said layer (a) to produce luminescence are measured in a space-resolved manner.

* * * * *